(12) United States Patent
Smith et al.

(10) Patent No.: US 6,582,950 B1
(45) Date of Patent: Jun. 24, 2003

(54) **C3 BINDING POLYPEPTIDE OF *STREPTOCOCCUS AGALACTIAE* GROUP B STREPTOCOCCUS**

(75) Inventors: Beverly L. Smith, Minneapolis, MN (US); Patricia Ferrieri, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 13 days.

(21) Appl. No.: 09/610,199

(22) Filed: Jul. 1, 2000

Related U.S. Application Data
(60) Provisional application No. 60/157,550, filed on Oct. 4, 1999, and provisional application No. 60/173,766, filed on Dec. 30, 1999.

(51) Int. Cl.$^7$ .......................... C12N 1/20; C12N 15/00; C12N 5/00; C07H 21/04
(52) U.S. Cl. ............................... 435/252.3; 435/320.1; 435/325; 536/23.7
(58) Field of Search ...................... 424/190.1; 435/69.3, 435/252.33, 253.4, 252.3, 320.1, 325; 536/23.7

(56) References Cited

U.S. PATENT DOCUMENTS
5,302,527 A * 4/1994 Birkett et al.
5,648,241 A * 7/1997 Michel et al.

FOREIGN PATENT DOCUMENTS
WO    WO 98/21337    5/1998

OTHER PUBLICATIONS

Teti et al., "Adherence of Group B Streptococci to Adult and Neonatal Epithelial Cells Mediated by Lipoteichoic Acid," *Infection and Immunity*, 1987 Dec.; vol. 55(12):3057–3064.
"A Group B Strep Vaccine!?!" Medical Advisory Board, Group B Strep Association (GBSA) [online]. [Retrieved on May 7, 1999]. Retrieved from the Internet: <URL:http://groupbstrep.org/gbs/vaccine.html>, 2 pages.
Altschul et al., "Gapped BLAST and PSI–BLAST: A new generation of protein database search programs," *Nucleic Acids Research*, 25(17):3389–3402 (1997).
Baker et al., "Correlation of Maternal antibody deficiency with susceptibility to neonatal group B streptococcal infection," *The New England Journal of Medicine*, 294(14):753–756 (1976).
Baker et al., "The Role of Complement and Antibody in Opsonophagocytosis of Type II Group B Streptococci," *The Journal of Infectious Diseases*, 154(1):47–54 (1986).
Baker et al., "Chapter 26: Group B Streptococcal Infections," *Infectious Diseases of the Fetus and Newborn Infant, Fourth Edition*, WB Saunders Co., Philadelphia, Title page, publication page, and pp. 980–1054 (1995).

Baynes et al., "A Preliminary Survey of Antibiotic Residues and Viable Bacteria in Milk from Three Caribbean Basin Countries," *Journal of Food Protection*, 62(2):177–180 (1999).
Bendel et al., "Distinct Mechanisms of Epithelial Adhesion for *Candida albicans* and *Candida tropicalis*," *The Journal of Clinical Investigation*, 92(4):1840–1849 (1993).
Bevanger et al., "A *Streptococcus agalactiae* R protein and analysed by polyclonal and monoclonal antibodies," *Acta Phathologica, Microbiologica Et Immunologica Scandinavica*, 103(1):731–736 (1995).
"BLAST 2 SEQUENCES," National Institutes of Health [online]. United States [retrieved Dec. 5, 2000]. Retrieved from the Internt: <URL:http://www.ncbi.nlm.nih.gov/blast/b12seq/b12.html>, 1 page.
Blumberg et al., "Invasive Group B Streptococcal Disease: The Emergence of Serotype V," *The Journal of Infectious Diseases*, 173(2):365–373 (1996).
Bohnsack et al., "Purification of the proteinase from group B streptococci that inactivates human C5a," *Biochemica et Biophysica Acta*. 1079(2):222–228 (1991).
Bohnsack et al., "Bacterial Evasion of the Antibody Response: Human IgG Antibodies Neutralize Soluble But Not Bacteria–Associated Group B Streptococcal C5a–ase," *The Journal of Infectious Diseases*, 165(2):315–321 (1992).
Brady et al., "Two Novel Antigens Associated with Group B Streptococci Identified by a Rapid Two–Stage Radioimmunoassay," *The Journal of Infectious Diseases*, 158(5):965–972 (1988).
Brady et al., "Identification of Non–Immunoglobulin A–Fe–Binding Forms and Low–Molecular–Weight Secreted Forms of the Group B Streptococcal β Antigen," *Infection and Immunity*, 57(5):1573–1581 (1989).
Brown et al., "Antimicrobial resistance in streptococcal species isolated from bovine mammary glands," *American Journal of Veterinary Research*, 51(12):2015–2018 (1990).
Campbell et al., "Influence of Serotype of Group B Streptococci on C3 Degradation," *Infection and Immunity*, 60(11):4558–4562 (1992).
Chait et al., "Weighing Naked Proteins: Practical, High–Accuracy Mass Measurement of Peptides and Proteins," *Science*, 257(5078):1885–1894 (1992).

(List continued on next page.)

*Primary Examiner*—Mark Navarro
(74) *Attorney, Agent, or Firm*—Mueting Raasch & Gebhardt

(57) ABSTRACT

This invention relates to the identification of a human complement C3 binding polypeptide and the nucleic acid which encodes the polypeptide from *Streptococcus agalactiae*. The polypeptide binds C3 and may be implicated in *S. agalactiae* adhesion and/or virulence. The polypeptide is conserved in mass in a variety of streptococcal isolates and is recognized by antibodies produced by humans exposed to or colonized with Group B Streptococcus.

17 Claims, 11 Drawing Sheets

OTHER PUBLICATIONS

Cheng et al., "A C–3 binding protein from *Streptococcus pneumoniae*," Abstract B–478, p. 110, *Abstract of the 97th Annual Meeting of the American Society for Microbiology*, Miami Beach, May 4–8, 3 pages (1997).

Cheng et al., "Novel Purification Scheme and Functions for a C–3 Binding Protein from *Streptococcus pneumoniae*," *Biochemistry*, 39(18):5450–5457 (May 9, 2999; published on Web Apr. 15, 2000).

Cleat et al., "Cloning and Expression in *Escherichia coli* of the Ibc Protein Genes of Group B Streptococci: Binding of Human Immunoglobulin A to the Beta Antigen," *Infection and Immunity*, 55(5):1151–1155 (1987).

"Clustal W: Multiple Sequence Alignment," Institute for Chemical Research, Kyoto University [online]. Kyoto, Japan [retrieved Dec. 6, 2000]. Retrieved from the Internet: <URI:http://www.clustalw.genome.adjp/>, 2 pages.

Dale et al., "Hyaluronate Capsule and Surface M Protein in Resistance to Opsonization of Group A Streptococci," *Infection and Immunity*, 64(5):1495–1501 (1996).

Farley et al., "A population–based assessment of invasive disease due to group B streptococcus in nonpregnant adults," *New England Journal of Medicine*, 328(25):1807–1811 (1993).

Farley, "Group B Streptococcal (GBS) Disease in Non–pregnant Adults," Medical Advisory Board, Group B Strep Association (GBSA) [online]. [Retrieved on May 7, 1999]. Retrieved from the Internet: URL: <http://groupbstrep.org/gbs/atRiskAdultScoop.html>, 2 pages.

Faxelius et al., "Neonatal septicemia due to group B streptococci—Perinatal risk factors and outcome of subsequent pregnancies," *Journal of Perinatal Medicine*, 16(5–6):423–430 (1988).

Ferrieri et al., "Production of Bacteremia and Meningitis in Infant Rats with Group B Streptococcal Serotypes," *Infection and Immunity*, 27(3):1023–1032 (1980).

Ferrieri, "Surface–Localized Protein Antigens of Group B Streptococci," *Reviews of Infectious Diseases*, 10(2):S363–S366 (1988).

Ferrieri, "Neonatal Susceptibility and Immunity to Major Bacterial Pathogens," *Reviews of Infectious Diseases*, 12(4):S394–S400 (1990).

Ferrieri et al., "Bacterial Surface Expression and Recognition of the IgA Binding Protein of Group B Streptococci," New Perspectives on Streptococci and Streptococcal Infections, Proceedings of the 11th Lancefield International Symposium on Streptococci and Streptococcal Diseases, Siena, Italy, 1990 *Zentralblatt für Bakteriologie. Supplement 22*, pp. 186–188 (1992).

Flores et al., "Molecular Species of R–Protein Antigens Produced by Clinical Isolates of Group B Streptococci," *Journal of Clinical Microbiology*, 27(5):1050–1054 (1989).

Flores et al., "Antibody profiles to the group B streptococcal beta antigen in maternal and infant paired sera," *Acta Pathologica Microbiologica et Immunologica Scandinavica*, 101(1):41–49 (1993).

Flores et al., "Characterization of Trypsin Resistant Proteins of Group B Streptococci (GBS)," *Pathogenic Streptococci: Present and Future*, A. Totlian, ed., Proceedings of the XII Lancefield International Symposium on Streptococci and Streptococcal Diseases, Lancer Publications, St. Petersburg, Russia, pp. 333–334 (1994).

Flores et al., "Molecular Diversity Among the Trypsin Resistant Surface Proteins of Group B Streptococci," *Zentralblatt für Bakteriologie*, 285(1):44–51 (1996).

Friedman et al., "Glycoprotein C of herpes simplex virus 1 acts as a receptor for the C3b complement component on infected ccells," *Nature*, 309(5969):633–635 (1984).

Friedman et al., "Immune Evasion Properties of Herpes Simplex Virus Type 1 Glycoprotein gC," *Journal of Virology*, 70(7):4253–4260 (1996).

Gravekamp et al., "Immunogenicity and Protective Efficacy of the Alpha C Protein of Group B Streptococci Are Inversely Related to the Number of Repeats," *Infection and Immunity*, 65(12):5216–5221 (1997).

"Group B Streptococcal Infections," Respiratory Diseases Branch, National Center for Infectious Diseases, Centers for Disease Control and Prevention, Atlanta [online]. Updated May 28, 1998 [retrieved on May 7, 1999] Retrieved from the Internet: <URL: http://www.cdc.gov/ncidod/diseases/bacter/strep_b.htm>, 3 pages.

"Group B Strep Vaccine Shows Promise in Clinical Studies," NIH News Release, National Institute of Allergy and Infectious Diseases, National Institutes of Health [online]. Nov. 20, 1996 [retrieved May 7, 1999]. Retrieved from the Internet: <URL:http://www.nih.gov/news/pr/nov96/niaid–20.htm>, 2 pages.

Hall et al., "Complement and Antibody in Neutrophil–Mediated Killing of Type V Group B Streptococcus," *The Journal of Infectious Diseases*, 170(1):88–93 (1994).

Harlow et al., *Antibodies: A Laboratory Manual*, Cold Spring Harbor Laboratory Press, NY, Title page, publication page, and table of contents only, 9 pages (1988).

Harrison et al., "Serotype Distribution of Invasive Group B Streptococcal Isolates in Maryland: Implications for Vaccine Formulation," *The Journal of Infectious Diseases*, 177(4):998–1002 (1998).

Hedéen et al., "Molecular characterization of an IgA receptor from group B streptococci: sequence of the gene, identification of a proline–rich region with unique structure and isolation of N–terminal fragments with IgA–binding capacity," *European Journal of Immunology*, 21(6):1481–1490 (1991).

Hill et al., "Group B streptococci inhibit the chemotactic activity of the fifth component of complement," *The Journal of Immunology*, 141(10):3551–3556 (1988).

Holmgren et al., "Mucosal Immunity: Implications for Vaccine Development," *Immunobiology*, 184(2/3):157–179 (1992).

Hostetter et al., "Binding of C3b proceeds by a transesterification reaction at the thiolester site," *Nature*, 298(5869):72–75 (1982).

Hostetter et al., "The Biochemistry of Opsonization: Central Role of the Reactive Thiolester of the Third Component of Complement," *The Journal of Infectious Diseases*, 150(5):653–661 (1984).

Hostetter, "Research Training in Infectious Diseases and Development," Grant No. 5T32HD007381–08 [online]. National Institute of Child Health and Human Development, the National Institutes of Health, project dates Jul. 1, 1990–Jun. 30, 2000 (abstract not available); retrieved from the Internet on Jun. 21, 2001 at <URL:http://commons.cit.nih.gov/crisp3/crisp_lib.getdoc?textkey=2655074&p_grant_num=5T32HD007381–08&p_query=&ticket=18470&p_audit_session_id=396922&p_keywords=>; 1 page.

Jacks–Weis et al., "Restricted Deposition of C3 on M+ Group A Streptococci: Correlation with Resistance to Phagocytosis," *The Journal of Immunology*, 128(4):1897–1902 (1982).

Jelínková, "On the question of type identification of group B streptococci and their distribution in human and bovine material," *Zentralbl. Bakteriol. Parasitenk. Infectionskr. Hyg. Abt.* 196:722–723 (1964).

Jerlström et al., "The IgA–binding β antigen of the c protein complex of Group B streptococci: sequence determination of its gene and detection of two binding regions," *Molecular Microbiology*, 5(4):843–849 (1991).

Keefe, "*Streptococcus agalactiae* mastitis: A review," *The Canadian Veterinary Journal*, 38(7):429–437 (1997).

Kubota et al., "Characterization of the C3 Receptor Induced by Herpes Simplex Virus Type 1 Infection of Human Epidermal Endothelial, and A431 Cells," *The Journal of Immunology*, 138(4):1137–1142 (1987).

Kvam et al., "Characterization of a Surface Protein of Group B Streptococci Resembling the α Antigen of the c Proteins," *Pathogenic Streptococci: Present and Future*, Lancer Publication, A. Totolian, ed., St. Petersburg, Russia, pp. 337–338 (1994).

Lachenauer et al., "A Protective Surface Protein from Type V Group B Streptococci Shares N–Terminal Sequence Homology with the Alpha C Protein," *Infection and Immunity*, 64(10):4255–4260 (1996).

Lachenauer et al., "Serotypes VI and VIII Predominate among Group B Streptococci Isolated from Pregnant Japanese Women," *The Journal of Infectious Diseases*, 179(4):1030–1033 (1999).

Lancefield et al., "Preparation and Properties of a Protein (R Antigen) Occurring in Streptococci of Group A, Type 28 and in Certain Streptococci of Other Serological Groups," *The Journal of Experimental Medicine*, 96:83–97 (1952).

Larsson et al., "Experimental Vaccination against Group B Streptococcus, an Encapsulated Bacterium, with Highly Purified Preparations of Cell Surface Proteins Rib and α," *Infection and Immunity*, 64(9):3518–3523 (1996).

Lindén et al., "Correlation between Low Levels of Maternal IgG Antibodies to R Protein and Neonatal Septicemia with Group B Streptococci Carrying R Protein," *International Archives of Allergy and Applied Immunity*, 71:168–172 (1983).

Madoff et al., "A Monoclonal Antibody Identifies a Protective C–Protein Alpha–Antigen Epitope in Group B Streptococci," *Infection and Immunity*, 59(1):204–210 (1991).

Madoff et al., "Phenotypic Diversity in the Alpha C Protein of Group B Streptococci," *Infection and Immunity*, 59(8):2638–2644 (1991).

Marques et al., "Prevention of C3 Deposition by Capsular Polysaccharide Is a Virulence Mechanism of Type III Group B Streptococci," *Infection and Immunity*, 60(10):3986–3993 (1992).

McGhee et al., "The mucosal immune system: from fundamental concepts to vaccine development," *Vaccine*, 10(2):75–88 (1992).

McNearney et al., "Herpes simplex virus glycoproteins gC–1 and gC–2 bind to the third component of complement and provide protection against complement–mediated neutralization of viral infectivity," *The Journal of Experimental Medicine*, 166:1525–1535 (1987).

Michel et al., "Cloned Alpha and Beta C–Protein Antigens of Group B Streptococci Elicit Protective Immunity," *Infection and Immunity*, 59(6):2023–2028 (1991).

Michel et al., "Large, identical, tandem repeating units in the C protein alpha antigen gene, bca, of group B streptococci," *Proceedings of the National Academy of Sciences USA*, 89(21):10060–10064 (1992).

Nizet et al., "Chapter 11: Molecular Pathogenesis of Group B Streptococcal Disease in Newborns," *Streptococcal Infections*, Stevens et al., eds., Oxford University Press, NY, Title page, publication page, and pp. 180–221 (2000).

Norris et al., "Characterizations of a *Trypanosoma cruzi* C3 Binding Protein with Functional and Genetic Similarities to the Human Complement Regulatory Protein, Decay–Accelerating Factor," *The Journal of Immunology*, 147(7):2240–2247 (1991).

Paoletti et al., "Group B Streptococcus Type II Polysaccharide–Tetanus Toxoid Conjugate Vaccine," *Infection and Immunity*, 60(10):4009–4014 (1992).

Payne et al., "The Relation of the Ibc Protein Antigen to the Opsonization Differences Between Strains of Type II Group B Streptococci," *The Journal of Infectious Diseases*, 15(4):672–681 (1985).

Payne et al., "Effect of Differences in Antibody and Complement Requirements on Phagocytic Uptake and Intracellular Killing of "c" Protein–Positive and –Negative Strains of Type II Group B Streptococci," *Infection and Immunity*, 55(5):1243–1251 (1987).

Payne et al., "Correlation of clinical and pathologic findings in early onset neonatal Group B streptococcal infection with disease severity and prediction of outcome," *The Pediatric Infectious Disease Journal*, 7(12):836–847 (1988).

"Prevention of Perinatal Group B Streptococcal Disease: A Public Health Perspective," Morbidity and Mortality Weekly Report, Epidemiology Program Office, Centers for Disease Control, United States Dept. of Health [online]. May 31, 1996, vol. 45(RR–7) [retrieved May 7, 1999]. Retrieved from the Internet: <URL:http://www.cdc.gov/epo/mmwr/preview/mmwrhtml/00043277.htm>, 22 pages.

Puentes et al., "Quantitative Analysis of C3 Deposition on Type II Group B Streptococci with the C Protein," New Perspectives on Streptococci and Streptococcal Infections, Proceedings of the 11th Lancefield International Symposium on Streptococci and Streptococcal Diseases, Siena, Italy, 1990, *Zentralblatt für Bakteriologie, Supplement 22*, pp. 470–472 (1992).

Rainard et al., "Opsonization of *Streptococcus agalactiae* of Bovine Origin by Complement and Antibodies against Group B Polysaccharide," *Infection and Immunity*, 60(11):4801–4808 (1992).

Rainard, "Activation of the classical pathway of complement by binding of bovine lactoferrin to unencapsulated *Streptococcus agalactiae*," *Immunology*, 79(4):648–652 (1993).

Rainard et al., "Deposition of Complement Components on *Streptococcus agalactiae* in Bovine Milk in the Absence of Inflammation," *Infection and Immunity*, 63(9):3422–3427 (1995).

Russell–Jones et al., "A Surface Receptor Specific for Human IgA on Group B Streptococci Possessing the Ibc Protein Antigen," *The Journal of Experimental Medicine*, 160(4):1467–1475 (1984).

Schneewind et al., "Sequence and Structural Characteristics of the Trypsin–Resistant T6 Surface Protein of Group A Streptococci," *Journal of Bacteriology*, 172(6):3310–3317 (1990).

Schuchat, "Epidemiology of Group B Streptococcal Disease in the United States: Shifting Paradigms," *Clinical Microbiology Reviews*, 11(3):497–513 (1998).

Shigeoka et al., "Strain Specificity of Opsonins for Group B Streptococci Types II and III," *Infection and Immunity*, 23(2):438–445 (1979).

Silva et al., "Characterization of a $C_3$ Receptor on the Envelope of *Schistosoma mansoni*," *The Journal of Immunology*, 151(12):7057–7066 (1993).

Smith et al., "Factors Modulating Pneumococcal Adhesion," Abstract 1097, *Pediatric Research, Program Issue*, 39(4 part 2):185A, 3 pages (1996).

Smith et al., "Characterization of a Pneumococcal Surface Protein that Binds Complement Protein C3 and its Role in Adhesion," Abstract D–122, p. 233, *Abstracts of the 98th General Meeting of the American Society for Microbiology*, Atlanta, May 17–21, 4 pages (1998).

Smith, *Characterization of a pneumococcal surface protein which binds complement protein C3 and its role in adhesion*, Doctoral Thesis, University of Minnesota, 112 pages (1998).

Smith et al., "Identification of the Gene Encoding GBbcA, a Group B Streptococcal Surface Protein that Binds Complement Protein C3," Abstract [online]. 101st General Meeting, American Society for Microbiology, Orlando, FL, May 20–24, 2001. Abstract presented May 24, 2001 [retrieved on May 14, 2001]. Retrieved from the Internet: <URL: http://www.abstractsonline.com/viewer/search.asp>, 3 pages.

Stålhammar–Carlemalm et al., "Protein Rib: A Novel Group B Streptococcal Cell Surface Protein that Confers Protective Immunity and Is Expressed by Most Strains Causing Invasive Infections," *The Journal of Experimental Medicine*, 177(6):1593–1603 (1993).

Suvorov et al., "Cloning of the Glutamine Synthetase Gene from Group B Streptococci," *Infection and Immunity*, 65(1):191–196 (1997).

Teti et al., "Adherence of Group B Streptococci to Adult and Neonatal Epithelial Cells Mediated by Lipoteichoic Acid," *Infection and Immunity*, 55(12):3057–3064 (1987).

Wästfelt et al., "Identification of a Family of Streptococcal Surface Proteins with Extremely Repetitive Structure," *The Journal of Biological Chemistry*, 271(31):18892–18897 (1996).

Wattiaux, "Topic # 5, Mastitis: The Disease and its Transmission," *Babcock Dairy Essentials, Topic Summaries from: Lactating and Milking, Technical Dairy Guide*, [online]. The Babcock Institute, International Dairy Research and Development, University of Wisconsin, copyright 1996 [retrieved Aug. 25, 1999]. Retrieved from the Internet <URL: http://babcock.cals.wisc.edu/>, 4 pages.

Wessels et al., "Immunogenicity in Animals of a Polysaccharide–Protein Conjugate Vaccine against Type III Group B Streptococcus," *The Journal of Clinical Investigation*, 86(5):1428–1433 (1990).

Wessels et al., "Immunogenicity and Protective Activity in Animals of a Type V Group B Streptococcal Polysaccharide–Tetanus Toxoid Conjugate Vaccine," *The Journal of Infectious Diseases*, 171(4):879–884 (1995).

Wessels et al., "Structural Properties of Group B Streptococcal Type III Polysaccharide Conjugate Vaccines That Influence Immunogenicity and Efficacy," *Infection and Immunity*, 66(5):2186–2192 (1998).

Wilkinson, "Type–Specific Antigens of Group B Type Ic Streptococci," *Infection and Immunity*, 4(5):596–604 (1971).

Wilkinson, "Comparison of Streptococcal R Antigens," *Applied Microbiology*, 24(4):669–670 (1972).

* cited by examiner

Surface expressed and secreted GBbcA binds C3

| mw | supernatants | trypsin extracts | |
|---|---|---|---|
| 200- | | | |
| 116- | | | |
| 97.6- | | | |
| 66- | | | ← GBbcA |
| 45- | | | |

Fig. 1

GBbcA conserved in many serotypes

Fig. 2

Purification of GBbcA Silver Stain

Fig. 3A

Purification of GBbcA Western

Fig. 3B

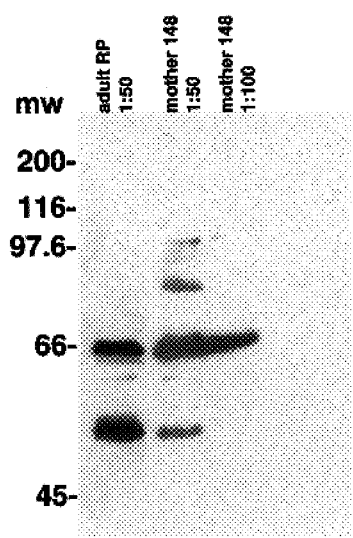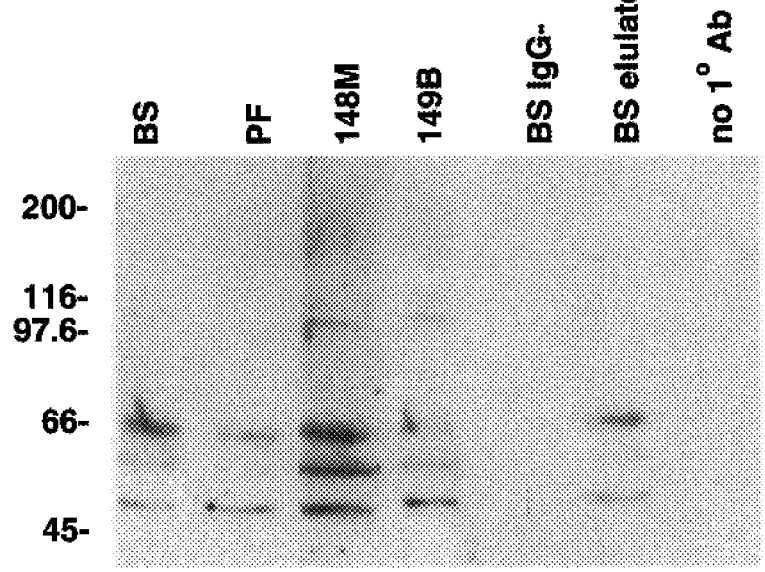
Fig. 5A                    Fig. 5B

Fig. 7

SEQ ID NO:1

DQTTSVQVNNQTGTSVDAAN

Fig. 8

SEQ ID NO:4

```
   1 TAATCAGACA GGCACTAGTG TGGATGCTAA TAATTCTTCC AATGAGACAA
  51 GTGCGTCAAG TGTGATTACT TCCAATAATG ATAGTGTTCA AGCGTCTGAT
 101 AAAGTTGTAA ATAGTCAAAA TACGGCAACA AAGGACATTA CTACTCCTTT
 151 AGTAGAGACA AAGCCAATGG TGGAAAAAAC ATTACCTGAA CAAGGGAATT
 201 ATGTTTATAG CAAAGAAACC GAGGTGAAAA ATACACCTTC AAAATCAGCC
 251 CCAGTAGCTT TCTATGCAAA GAAAGGTGAT AAAGTTTTCT ATGACCAAGT
 301 ATTTAATAAA GATAATGTGA ATGGATTTC ATATAAGTCT TTTGGTGGCG
 351 TACGTCGATA CGCAGCTATT GAGTCACTAG ATCCATCAGG AGGTTCAGAG
 401 ACTAAAGCAC CTACTCCTGT AACAAATTCA GGAAGCAATA ATCAAGAGAA
 451 AATAGCAACG CAAGGAAATT ATACATTTTC ACATAAAGTA GAAGTAAAAA
 501 ATGAAGCTAA GGTAGCGAGT CCAACTCAAT TTACATTGGA CAAAGGAGAC
 551 AGAATTTTTT ACGACCAAAT ACTAACTATT GAAGGAAATC AGTGGTTATC
 601 TTATAAATCA TTCAATGGTG TTCGTCGTTT TGTTTTGCTA GGTAAAGCAT
 651 CTTCAGTAGA AAAAACTGAA GATAAAGAAA AAGTGTCTCC TCAACCACAA
 701 GCCCGTATTA CTAAAACTGG TAGACTGACT ATTTCTAACG AAACAACTAC
 751 AGGTTTTGAT ATTTTAATTA CGAATATTAA AGATGATAAC GGTATCGCTG
 801 CTGTTAAGGT ACCGGTTTGG ACTGAACAAG GAGGGCAAGA TGATATTAAA
 851 TGGTATACAG CTGTAACTAC TGGGGATGGC AACTACAAAG TAGCTGTATC
 901 ATTTGCTGAC CATAAGAATG AGAAGGGTCT TTATAATATT CATTTATACT
 951 ACCAAGAAGC TAGTGGGACA CTTGTAGGTG TAACAGGAAC TAAAGTGACA
1001 GTAGCTGGAA CTAATTCTTC TCAAGAACCT ATTGAAAATG GTTTACCAAA
1051 GACTGGTGTT TATAATATTA TCGGAAGTAC TGAAGTAAAA AATGAAGCTA
1101 AAATATCAAG TCAGACCCAA TTTACTTTAG AAAAGGTGA CAAAATAAAT
1151 GACAAGTTTC CCC
```

Fig. 10

SEQ ID NO:5

```
  1  MVTSPVFADQ TTSVQVNNQT GTSVDANNSS NETSASSVIT SNNDSVQASD
 51  KVVNSQNTAT KDITTPLVET KPMVEKTLPE QGNYVYSKET EVKNTPSKSA
101  PVAFYAKKGD KVFYDQVFNK DNVKWISYKS FGGVRRYAAI ESLDPSGGSE
151  TKAPTPVTNS GSNNQEKIAT QGNYTFSHKV EVKNEAKVAS PTQFTLDKGD
201  RIFYDQILTI EGNQWLSYKS FNGVRRFVLL GKASSVEKTE DKEKVSPQPQ
251  ARITKTGRLT ISNETTTGFD ILITNIKDDN GIAAVKVPVW TEQGGQDDIK
301  WYTAVTTGDG NYKVAVSFAD HKNEKGLYNI HLYYQEASGT LVGVTGTKVT
351  VAGTNSSQEP IENGLPKTGV YNIIGSTEVK NEAKISSQTQ FTLEKGDKIN
401  YDQVLTADGY QWISYKSYSG VRRYIPVKKL TTSSEKAKDE ATKPT
```

SEQ ID NO:2

IATQGNYTFSHK

*Fig. 11*

SEQ ID NO:3

NYDQVLHADGYS

SEQ ID NO:6

```
   1  ATGGTCACAA GTCCTGTTTT TGCGGATCAA ACTACATCGG TTCAAGTTAA
  51  TAATCAGACA GGCACTAGTG TGGATGCTAA TAATTCTTCC AATGAGACAA
 101  GTGCGTCAAG TGTGATTACT TCCAATAATG ATAGTGTTCA AGCGTCTGAT
 151  AAAGTTGTAA ATAGTCAAAA TACGGCAACA AAGGACATTA CTACTCCTTT
 201  AGTAGAGACA AAGCCAATGG TGGAAAAAAC ATTACCTGAA CAAGGGAATT
 251  ATGTTTATAG CAAAGAAACC GAGGTGAAAA ATACACCTTC AAAATCAGCC
 301  CCAGTAGCTT TCTATGCAAA GAAAGGTGAT AAAGTTTTCT ATGACCAAGT
 351  ATTTAATAAA GATAATGTGA AATGGATTTC ATATAAGTCT TTTGGTGGCG
 401  TACGTCGATA CGCAGCTATT GAGTCACTAG ATCCATCAGG AGGTTCAGAG
 451  ACTAAAGCAC CTACTCCTGT AACAAATTCA GGAAGCAATA ATCAAGAGAA
 501  AATAGCAACG CAGGGAAATT ATACATTTTC ACATAAAGTA GAAGTAAAAA
 551  ATGAAGCTAA GGTAGCGAGT CCAACTCAAT TTACATTGGA CAAAGGAGAC
 601  AGAATTTTTT ACGACCAAAT ACTAACTATT GAAGGAAATC AGTGGTTATC
 651  TTATAAATCA TTCAATGGTG TTCGTCGTTT TGTTTTGCTA GGTAAAGCAT
 701  CTTCAGTAGA AAAAACTGAA GATAAAGAAA AAGTGTCTCC TCAACCACAA
 751  GCCCGTATTA CTAAAACTGG TAGACTGACT ATTTCTAACG AAACAACTAC
 801  AGGTTTTGAT ATTTTAATTA CGAATATTAA AGATGATAAC GGTATCGCTG
 851  CTGTTAAGGT ACCGGTTTGG ACTGAACAAG GAGGGCAAGA TGATATTAAA
 901  TGGTATACAG CTGTAACTAC TGGGGATGGC AACTACAAAG TAGCTGTATC
 951  ATTTGCTGAC CATAAGAATG AGAAGGGTCT TTATAATATT CATTTATACT
1001  ACCAAGAAGC TAGTGGGACA CTTGTAGGTG TAACAGGAAC TAAAGTGACA
1051  GTAGCTGGAA CTAATTCTTC TCAAGAACCT ATTGAAAATG GTTTACCAAA
1101  GACTGGTGTT TATAATATTA TCGGAAGTAC TGAAGTAAAA AATGAAGCTA
1151  AAATATCAAG TCAGACCCAA TTTACTTTAG AAAAAGGTGA CAAAATAAAT
1201  TATGATCAAG TATTGACAGC AGATGGTTAC CAGTGGATTT CTTACAAATC
1251  TTATAGTGGT GTTCGTCGCT ATATTCCTGT GAAAAAGCTA ACTACAAGTA
1301  GTGAAAAAGC GAAAGATGAG GCGACTAAAC CGACTAG
```

C3 BINDING POLYPEPTIDE OF *STREPTOCOCCUS AGALACTIAE* GROUP B STREPTOCOCCUS

CROSS REFERENCE TO RELATED APPLICATIONS

This application claims the benefit under 35 U.S.C. §119 (e) of U.S. Provisional Patent Application No. 60/157,550, filed on Oct. 4, 1999, and U.S. Provisional Patent Application No. 60/173,766, filed on Dec. 30, 1999, both of which are hereby incorporated by reference.

FIELD OF THE INVENTION

This invention relates to *Streptococcus agalactiae*, Group B Streptococcus, and in particular this invention relates to the identification of a *S. agalactiae* polypeptide and a gene encoding it that may be implicated in Group B streptococcal adhesion and/or virulence. The *S. agalactiae* polypeptide according to the invention demonstrates binding of human complement C3.

BACKGROUND OF THE INVENTION

*Streptococcus agalactiae*, or group B Streptococcus (GBS), is a leading cause of infant mortality. GBS encompasses an estimated prevalence of several thousand cases per year resulting in an annual mortality rate in the United States between about 10% and 15% (Schuchat, Clin. Micro Rev., 11(3):497–513 (1998)). Although worldwide prevalence is known, insufficient specific epidemiological data is not readily available.

Several virulence factors have been reported in GBS,. In addition to the streptococcal capsule, which is an important virulence factor, lipotechoic acid, a glycerol-phosphate polymer extending throughout the cell wall, is a virulence factor that may mediate adhesion (Teti et al., *Infection and Immunity*, 55(12):3057–3064 (1987)). Proteins such as hyaluronate lyase, cAMP factor, proteases, nucleases, hippuricase, neuraminidase, hemolysin, and C5a peptidase are expressed from GBS and many have been shown to be virulence factors (Nizet et al., *Streptococcal Infections*, Stevens D L and Kaplan E L, Eds. (2000); Bohnsack et al., *Biochimica et Biophysica Acta*, 1079:222–228 (1991)). In short, many studies are underway to define virulence factors molecularly by the mutation of genes encoding these proteins under question and the examination in assays for biological function.

The C proteins, or antigens, have been further characterized as alpha proteins (Madoff et al., *Infection and Immunity*, 59(1):204–210 (1991)), as beta proteins (Russell-Jones et al., *J. Exp Med.* 160:1467–1475 (1984); Jerlstrom et al., *Mol. Microbiol.*, 5:843–849 (1991)), and as gamma and delta proteins (Brady et al., *Infect. Immun.*, 57:1573–1581 (1989)). Not much is known about gamma and delta C proteins as there have not been further reports since their identification. The alpha C protein, which is resistant to the protease trypsin, varies in molecular weight from about 30 kDa to about 190 kDa in a ladder-like array (Madoff et al., *Infection and Immunity*, 59(1):204–210 (1991)). The beta C protein, which is sensitive to the protease trypsin and typically exhibits less variability in size (molecular weight of about 14 kDa to about 145 kDa), is typically expressed as a single 130 kDa protein that is capable of binding human IgA (Russell-Jones et al., *J. Exp. Med.*, 160:1467–1475 (1984)).

C proteins are suggested to contribute to GBS virulence in infant rat models (Ferrieri et al., *Infection and Immunity*, 27(3):1023–1032 (1980)) and some GBS strains without C protein are more easily killed in an opsonophagocytic bactericidal assay (Payne and Ferrieri, *J Infectious Diseases*, 151(4):672–681 (1985)). Other alpha-like proteins have also been reported (Kvam et al, *Pathogenic Streptococci: Present and Future*, Lancer Publication (A. Totolian (Ed.), St. Petersburg, Russia (1994)), and are under further investigation.

R proteins, or antigens, first identified by Lancefield and Perlman, were further characterized (Wilkinson, *Infection and Immunity*, 4(5):596–604 (1971); Bevanger et al., *APMIS*, 103:731–736 (1995)) and later determined to resemble the alpha C proteins in multiple molecular weight forms, resistance to trypsin, and imunogenicity (Wilkinson, *Infection and Immunity*, 4(5):596–604 (1971); Madoff et al., *Infection and Immunity*, 59(8):2638–2644 (1991); Flores and Ferrieri, *Zbl.Bakt.*, 285:44–51 (1996)). The R proteins were identified as separate proteins R1, R2, R3, R4, and R5 by various investigators (Flores and Ferrieri, *Zbl.Bakt.*, 285:44–51 (1996); Wilkinson, *Applied Microbiology*, 24(4):669–670 (1972)). Finally, a similar protein designated "Rib" (Stalhammar-Carlemalm et al., *J. Experimental Medicine*, 177:1593–1603 (1993)), while proposed as an individual entity, is suspected to be an R protein (Flores and Ferrieri, *Zbl.Bakt.*, 285:44–51 (1996)). Whereas these proteins have been characterized and grouped phenotypically, further molecular characterization of these groups is underway as well as the identification of new surface proteins unique in structure and biological functions.

Human mothers colonized with GBS represent approximately 15–35% of the U.S. population, and are known to transmit GBS to their infants before birth. This results in an incidence of neonatal GBS disease at a rate of 1 to 2 infants per 1,000 live births, and a mortality after birth due to complications of bacteremia/sepsis, and/or meningitis, or GBS infection in utero possibly resulting in stillbirth (Schuchat, *Clin. Micro Rev.*, 11(3):497–513 (1998)). Even infant survivors of GBS meningitis suffer from resulting chronic neurologic injury ranging from deafness, learning disabilities, as well as motor, sensory, and cognitive impairment (Baker et al., *Infectious Diseases of the Fetus and Newborn Infant.*, (4th Ed.) W.B. Saunders Company (1995)). Currently, antibiotic prophylaxis in parturients is the recommended approach for prevention of neonatal disease; however, this approach may be ineffective. With the resurgence of antibiotic resistance in other streptococcal species, a similar plight in group B Streptococcus may occur, making the need for effective vaccines urgent. It is known that infants do not make sufficient protective antibodies to GBS capsular polysaccharides, and maternal antibodies to capsule may not be sufficient for placental transfer and protection. Even after vaccination with current polysaccharide vaccines, antibody titers are low in individuals at greatest risk for colonization and severe infection (Linden et al., *Int. Archs. Allergy Appl. Immun.*, 71:168–172 (1983)).

In addition to infants, other persons at high risk for GBS infection are the elderly and immuno-compromised persons (Farley et al., *N. Engl. J. Med.*, 328:1807–1811 (1993)). Although currently under investigation, sufficient data on antibody production in the elderly is lacking. Antibody titers, however, may also be deficient in this age group, and it remains possible that immunization may protect elderly against invasive GBS disease (Schuchat, *Clin. Micro Rev.*, 11(3):497–513 (1998)).

In addition to the problems confronting humans, many GBS strains are known to cause bovine mastitis in cows resulting in a monetary loss to dairy farmers as well as GBS strains known to cause mastitis in goats and other lactating mammals. GBS in cows is currently controlled by prophylactic antibiotic treatment (Keefe, *Can. Vet. J.,* 38(7):429–37 (1997)). Concerns, however, have been raised regarding residual antimicrobials in milk from this prophylactic treatment, as well as the growing antimicrobial resistance in GBS strains (Baynes et al., *J Food Prot.,* 62(2):177–80 (1999)).

In response to the dilemmas described above, protein conjugate vaccines have been developed, and several are currently in clinical trials (Larsson et al., *Infection and Immunity,* 64(9):3518–3523 (1996)). Proteins that could be used as components of vaccines, as conjugates coupled to capsular polysaccharide (which act as adjuvants to boost antibody response), or as whole protein vaccine candidates themselves are under investigation. Problems existing with some protein conjugate vaccines include variability in protein structure resulting in a ladder-like array of proteins (Gravekamp et al., *Infection and Immunity.,* 65(12):5216–5221 (1997)).

Another significant issue is that current protein conjugate vaccines are restricted to the GBS serotypes prevalent only in the United States. This includes mainly types I, II, III, and V, in contrast to a range of nine different serotypes that are able to colonize and cause invasive disease (Harrison et al., *J. of Infectious Disease,* 177:998–1002 (1998)). Since 1990, four new capsular serotypes IV, V, VI, and VII have been identified as associated with human invasive disease, with an increasing prevalence in type V (Blumberg et al., *J. of Infectious Disease* 173:365–73 (1996)). In addition, types VI and VIII are the most common serotypes in Japan not protected against by current vaccines (Lachenauer et al., *J Infectious Disease,* 179:1030–1033 (1999)).

Thus, a need exists for polypeptides that can be employed in immunogenic compositions and vaccines, for example.

SUMMARY OF THE INVENTION

A novel group B streptococcal protein GBbcA, Group B binds complement C3 has been identified. GBbcA is a surface polypeptide found in all group B streptococcalstrains and serotypes examined to date that bind complement protein C3. In addition to its surface expression and conservation, it appears to be immunogenic in both rabbits and humans, thus fulfilling certain criteria for vaccine candidacy. In addition, data suggests that antibodies are placentally transferred from mother to neonate, which is especially important in the development of vaccines and immunogenic compositions for pediactric diseases.

The present invention relates to the identification and isolation of a 60 kDa±10 kDa polypeptide as determined by electrophoresis on a 7.5% SDS-PAGE gel. A preferred polypeptide is named GBbcA, and can be isolated from *S. agalactiae* strains that bind to human complement protein C3. The polypeptide GBbcA (SEQ ID NO:5, FIG. 10) has an internal peptide region (SEQ ID NO:2, FIG. 11).

Accordingly, the present invention provides an isolated polypeptide having at least 50% amino acid identity with the polypeptide represented by SEQ ID NO:5. The isolated polypeptide of the invention can be longer, shorter, or of the same length of amino acids as the polypeptide represented by SEQ ID NO:5. Preferably, the polypeptide binds human complement C3 and is isolated from *S. agalactiae*. Additionally, the polypeptide of the invention can be a recombinant polypeptide. The polypeptide preferably has a molecular weight of about 50 kDa to about 70 kDa as determined by SDS-polyacrylamide gel electrophoresis.

The present invention further provides a polypeptide that binds human complement C3 containing amino acids 365–370 of SEQ ID NO:5. Further, an isolated polypeptide may include amino acids represented by SEQ ID NO:1 wherein the polypeptide binds human complement C3.

In another aspect of the invention, an isolated polypeptide, which has a molecular weight of about 50 kDa to about 70 kDa as determined by SDS-polyacrylamide gel electrophoresis; is isolated from *S. agalactiae*, and binds human complement C3, is provided. A preferred polypeptide having these characteristics is represented by SEQ ID NO:5. Further, an isolated polypeptide containing the amino acids represented by SEQ ID NO:5 wherein the polypeptide binds human complement C3 is also provided.

In yet another aspect of the invention, an isolated polypeptide that binds human complement C3, wherein nucleic acid encoding the polypeptide hybridizes to at least a portion of at least one of the nucleic acid fragments represented by SEQ ID NO:6 or SEQ ID NO:4 or their complementary strands under standard hybridization conditions, is provided. The nucleic acid fragments can be longer, shorter, or of the same length of nucleotides as the polynucleotides represented by SEQ ID NO:6 or SEQ ID NO:4. Preferably, the nucleic acid encoding the polypeptide has at least 50% nucleic acid identity to the nucleic acid fragments represented by SEQ ID NO:4 or SEQ ID NO:6.

In another aspect of the invention, an isolated polypeptide of about 50 kDa to about 70 kDa from *S. agalactiae* that binds human complement C3 is provided.

The present invention further provides an immune system stimulating composition containing an effective amount of an immune system stimulating polypeptide, wherein the polypeptide has at least 50% amino acid identity with the polypeptide represented by SEQ ID NO:5 and binds human complement C3. Preferably, the polypeptide of the immune system stimulating composition is isolated from *S. agalactiae*. Additionally, the immune system stimulating composition can contain at least one other immune system stimulating polypeptide isolated from *S. agalactiae*.

In another aspect of the invention, an immune system stimulating composition containing an effective amount of a polypeptide, wherein nucleic acid encoding the polypeptide hybridizes to at least a portion of at least one of the nucleic acid fragments represented by SEQ ID NO:6 or SEQ ID NO:4 or their complementary strands under standard hybridization conditions is provided. Preferably, an immune system stimulating composition according to the invention contains an effective amount of at least a portion of the about 50 kDa to about 70 kDa polypeptide that is effective to treat a mammal against *S. agalactiae* colonization or infection, and a pharmaceutically acceptable carrier.

In yet another aspect of the invention, an antibody that binds to a polypeptide which binds human complement C3 having at least 50% amino acid identity with the polypeptide represented by SEQ ID NO:5 is provided. The antibody can be obtained from a mouse, a rat, a goat, a chicken, a human, or a rabbit. Preferably, the antibody is a monoclonal antibody.

The present invention further provides an antibody that binds a polypeptide, wherein nucleic acid encoding the polypeptide hybridizes to at least a portion of at least one the nucleic acid fragments represented by SEQ ID NO:6 or SEQ ID NO:4 or their complementary strands under standard hybridization conditions.

In another aspect of the invention, an isolated nucleic acid fragment that hybridizes to at least a portion of at least one the nucleic acid fragments represented by SEQ ID NO:6 or SEQ ID NO:4 or their complementary strands under standard hybridization conditions is provided. The nucleic acid fragment can be isolated from *S. agalactiae* and preferably encodes a polypeptide represented by SEQ ID NO:5. Preferably, the polypeptide binds human complement C3. The nucleic acid fragment of the invention can further be provided in a nucleic acid vector, such as an expression vector and is capable of producing a polypeptide as described herein. Nucleic acid fragments of the invention can be provided in a cell, such as a bacterium or a eukaryotic cell.

In another aspect of the invention, an isolated nucleic acid having at least 50% nucleic acid identity to the nucleic acid fragments represented by SEQ ID NO:6 or SEQ ID NO:4 and which hybridizes under standard hybridization conditions to at least a portion of at least one of the nucleic acid fragments represented by SEQ ID NO:6 or SEQ ID NO:4 or their complementary strands is provided.

Also provided is an isolated polynucleotide encoding a polypeptide containing the amino acids represented by SEQ ID NO:5. Further provided is an isolated nucleic acid fragment containing the nucleic acid fragments represented by SEQ ID NO:6 or SEQ ID NO:4 or their complementary strands. Additionally, an RNA transcribed by a double-stranded nucleic acid containing nucleic acid fragments represented by SEQ ID NO:6 or SEQ ID NO:4 or their complementary strands is provided.

In yet another aspect of the invention, a method for producing an immune response to *S. agalactiae* in a mammal having the steps of administering a composition containing an effective amount of a polypeptide to a mammal, wherein nucleic acid encoding the polypeptide hybridizes to at least a portion of at least one of the nucleic acid fragments represented by SEQ ID NO:6 or SEQ ID NO:4 or their complementary strands under standard hybridization conditions in a pharmaceutically acceptable carrier to yield an immune response is provided. The immune response can be a B cell response, a T cell response, an epithelial cell response, or an endothelial cell response. Additionally, the composition may further contain at least one other immune system stimulating polypeptide from *S. agalactiae*.

The present invention also provides a method for producing an immune response to *S. agalactiae* in a mammal having the steps of administering a composition containing an effective amount of a polypeptide to a mammal, wherein nucleic acid encoding the polypeptide hybridizes to at least a portion of at least one of the nucleic acid fragments represented by SEQ ID NO:6 or SEQ ID NO:4 or their complementary strands under standard hybridization conditions in a pharmaceutically acceptable carrier to yield an immune response.

In yet another aspect of the invention, an antigenic conjugate molecule having a capsular polysaccharide derived from Group B Streptococcus and a polypeptide containing the amino acids represented by SEQ ID NO:5 wherein two or more side chains terminating in sialic acid residues of the polysaccharide component are each linked through a secondary amine bond to polypeptide is provided. Also provided is a method of immunizing a mammal wherein a vaccine containing the antigenic conjugate molecule is administered in an effect amount to a mammal at risk for being colonized or infected by Group B Streptococcus.

The present invention also provides a method for detecting Group B Streptococcus in a mammal containing, (a) contacting an amount of an isolated nucleic acid from a biological sample from a mammal exposed to or afflicted with Group B Streptococcus colonization or infection with an amount of at least two oligonucleotides under conditions effective to amplify the nucleic acid so as to yield an amount of an amplified nucleic acid, wherein at least one oligonucleotide is specific for the nucleic acid represented by either SEQ ID NO:4 or SEQ ID NO:6 or their complementary strands; and (b) detecting the presence of the amplified nucleic acid, wherein the presence of the amplified nucleic acid is indicative of a mammal exposed to or afflicted with Group B Streptococcus colonization or infection.

As used herein the terms "isolated and/or isolatable," when referring to a nucleic acid fragment means that it has been removed from a sample in which it is originally found. This may include concentrating the desired nucleic acid fragment without necessarily removing any other materials. It also includes separating nucleic acid fragments from cells expressing the nucleic acid fragments or from other materials, such as cellular components, polypeptides, lipids, salts, etc. In referring to a polypeptide that is "isolated and/or isolatable," either removed from its natural environment or synthetically derived. Preferably, it is meant that the polypeptide is purified, i.e., essentially free from any other polypeptides and associated cellular products or other impurities.

"Polypeptide" as used herein refers to a polymer of amino acids and does not refer to a specific length of a polymer of amino acids. Thus, for example, the terms peptide, oligopeptide; protein, and enzyme are included within the definition of polypeptide. This term also includes post-expression modifications of the polypeptide, for example, glycosylations, acetylations, phosphorylations, and the like.

"Nucleic acid fragment" or "polynucleotide" as used herein refers to a linear polymeric form of nucleotides of any length, either ribonucleotides or deoxynucleotides, and includes both double- and single-stranded DNA and RNA. A nucleic acid fragment may include both coding and noncoding regions that can be obtained directly from a natural source (e.g., a microorganism), or can be prepared with the aid of recombinant or synthetic techniques. A nucleic acid according to the invention may be equivalent to this nucleic acid fragment or it can include this fragment in addition to, one or more other nucleotides. For example, the nucleic acid fragment of the invention can be a vector, such as an expression or cloning vector.

"Percentage amino acid identity" refers to a comparison of the amino acids of two polypeptides as described herein. Amino acid alignment may be determined, for example, using the sequence alignment program CLUSTAL W available on the Internet at genome.ad.jp/SIT/CLUSTALW.html and percent amino acid identity may be determined by BLAST at National Center for Biotechnology Information (NCBI) website available on the Internet at ncbi.nlm.nih.gov.

"Percentage nucleic acid identity" refers to a comparison of the nucleic acids of two nucleic acid fragments as described herein. Nucleic acid alignment may be determined, for example, using a nucleic acid alignment program available on the Internet at genome.ad.jp/SIT/CLUSTALW.html and percent nucleic acid identity may be determined by BLAST at National Center for Biotechnology Information (NCBI) website available on the Internet at ncbi.nlm.nih.gov.

"Standard hybridization conditions" refers to hybridizing conditions of prehybridization for 1 hour at 62° C. in hybridization solution (5×SSC (1×SSC is 0.15 M NaCl, 0.015 M sodium citrate), 0.02% sodium dodecyl sulfate (SDS), 0.1% N-lauroylsarcosine, 1% Blocking Reagent) and subsequent hybridization with the 1337 basepair gbbcA digoxygenin-probe (1000 ng/ml) in the hybridization solution overnight at 62° C. and two stringency washes with 2×SSC, 0.1% SDS for 5 minutes at room temperature and once with 0.5×SSC, 0.1% SDS for 15 minutes at 62° C. followed by a digoxygenin detection protocol pursuant to manufacturer's directions (Roche Molecular Biochemicals, Indianapolis, Ind.).

BRIEF DESCRIPTION OF THE FIGURES

FIG. 1 shows a Western blot demonstrating surface expressed and secreted C3-binding protein GBbcA from strain 76-043.

FIG. 2 shows a Western blot demonstrating conservation of secreted C3-binding protein GBbcA in serotypes I, II, III, IV, V, and non-typeable (NT).

FIG. 3 shows a silver stain (A) and Western blot (B) demonstrating purification of C3-binding protein GBbcA from strain 76-043 using a C3 affinity column prepared from commercially available C3 (Calbiochem, LaJolla, Calif.).

FIG. 4 shows a Western blot demonstrating antibodies against GBbcA in rabbit umn62 antiserum.

FIGS. 5A and 5B show a Western blot demonstrating antibodies in adult antisera. In 5A, immunogenicity was evident in adults using human antiserum from normal adult RP and colonized mother 148. In 5B, immunogenicity was evident using human antiserum from adults BS, PF, and mother 148. BS IgG antiserum passed over a protein A column and depleted of IgG acted as a negative control and did not detect GBbcA, whereas BS eluate contained IgG recovered from elution which detected GBbcA.

FIG. 6 shows a Western blot demonstrating antibodies against GBbcA in maternal antiserum and antibodies against GBbcA in neonatal cord sera suggesting placental transfer.

FIG. 7 is the amino acid sequence SEQ ID NO:1 used to create degenerate primer SEQ ID NO:7.

FIG. 8 is the nucleic acid PCR product of gbbcA generated by degenerate primers SEQ ID NO:7 and SEQ ID NO:8 containing 1163 base pairs (SEQ ID NO:4).

FIG. 9 shows an agarose gel of PCR generated products from degenerate oligonucleotide primers and sequences. Agarose gel of Ia, Ib, Ia/c, II, III, IV, V, VI, VII, and VIH PCR products from primers N-terminal and peak 79.

FIG. 10 is the predicted amino acid sequence represented by SEQ ID NO:5 of a 60 kDa±10 kDa polypeptide from *S. agalactiae* according to the invention derived from gbbcA.

FIG. 11 shows internal amino acids (SEQ ID NO:2) of a 60. kDa±10 kDa polypeptide from *S. agalactiae.*

FIG. 12 shows amino acid sequence SEQ ID NO:3 used to create degenerate primer SEQ ID NO:8.

FIG. 13 shows the sequence of a nucleic acid fragment of gbbcA, which contains 1337 bases from the open reading frame beginning with ATG and is represented by SEQ ID NO:6.

DETAILED DESCRIPTION OF THE PREFERRED EMBODIMENTS

The present invention provides a Group B Streptococcus (GBS) surface polypeptide that binds C3. The polypeptide has a molecular weight of about 60 kDa±10 kDa following electrophoresis,,as determined on a 7.5% SDS-PAGE gel and in a preferred embodiment is referred to as "GBbcA." The C3 binding polypeptide of this invention can be isolated from *S. agalactiae.*

GBbcA is a new, undisclosed polypeptide that binds human complement C3 and can be isolated from *S. agalactiae*. In the non-immune host, C3, is the central mechanism of host defense. C3 is composed of an α-chain having a molecular weight of about 115 kDa, and a β-chain having a molecular weight of about 75 kDa, joined by a disulfide bond. It is through this bond that opsonization occurs (Hostetter et al., *Nature,* 298:72–75 (1982)). The deposition of opsonic C3b on *Streptococcus pneumoniae* is well characterized and the non-covalent binding of C3 to pneumococci has recently been described by a surface associated protein PbcA (pneumococcal binds complement protein C3, molecular weight of 90 kDa±5 kDa) (Smith, B., *Characterization of a pneumococcal surface protein which binds complement protein C3 and its role in adhesion,* Univ. of Minnesota, Dissertation, pages 1–77 (1998); Cheng and Hostetter, *American Society for Microbiology 97$^{th}$ General Meeting,* Abstract B1478 (Miami, Fla. (1997)). This surface associated protein is also known as CbpA (complement binding protein A). Disruption of the internal thiolester bond by nucleophilic attack, such as the incorporation of methylamine, yields a thiolester-modified C3 molecule. This molecule retains its native form except for the conformational change which exposes and disrupts the thiolester, thus preventing further covalent interactions and enabling the study of non-covalent interactions of C3 and different streptococcal species.

The opsonization of *S. agalactiae*, has also been well characterized. First in the participation of the classical complement pathway to opsonize GBS types I, II, and many type m strains, and second, in the alternative complement pathway-mediated opsonization and phagocytosis facilitated by specific antibody to type 1II (Baker et al., *J. of Infectious Disease* 154(1):47–54 (1986)), or type V (Hall et al., J Infectious Disease, 170:88–93 (1994)). Interference of C3 deposition occurs from heavy encapsulation of the sialylated polysaccharide capsule. It is possible that the presence of C antigen on type II strains may limit C3 deposition as suggested by fluorescent antibody detection of decreased C3 deposition on the surface of GBS strains expressing C protein (Payne and Ferrieri, *Infect. Immun.,* 55(5): 1243–1251 (1987)). Thus, with the identification of nonopsonic binding of C3 in GBS, a new means of virulence and interference of opsonization may be identified.

Binding of complement proteins has been reported in many different types of organisms and may play many different roles including a new paradigm for virulence and for resistance to host immune responses. In signal transduction, the binding of C3 could induce signals for biochemical synthesis such as in the parasite *Schistosoma mansoni,* wherein C3 bound to a parasitic receptor and stimulated synthesis of the parasitic envelope (Silva et al., *J. Immunology,* 151(12):7057–7066 (1993)). Likewise, the binding of C3 is important in adhesive interactions. For example, in fungal adhesion, a C3 fragment iC3b bound the fungal receptor int1 on *Candida albicans,* and iC3b expressed on the surface of epithelial cells was shown of functional importance in the adhesion of *C. albicans* to human cervical epithelium (Bendel et al., *J. Clin. Invest.,* 92:1840–1849 (1993)). In bacterial adhesion, C3 binds to the protein, PbcA, in *S. pneumoniae.* C3 has previously been shown to act as a ligand in pneumococcal adhesion, and PbcA which binds C3 acts as an adhesin and has been suggested to play a role in evasion of host defenses (Smith,

Figure 4:
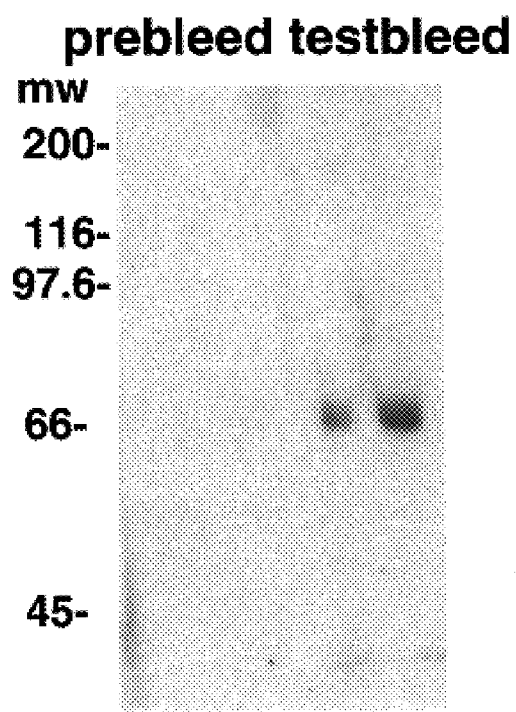

B., *Characterization of a pneumococcal surface protein which binds complement protein C3 and its role in adhesion*, Univ. of Minnesota, Dissertation, pages 1–77 (1998)).

Many organisms have developed mechanisms which regulate C3 covalent binding to prevent C3 deposition and subsequent clearance such as demonstrated by the complement regulator protein (CRP) in *Trypanosoma cruzi*, which binds C3b and C4b, inhibits C3 convertase formation, and yields resistance to complement mediated lysis (Norris et al., *J. Immunology*, 147(7):2240–2247 (1991)). For some viruses such as herpes simplex virus (HSV), the presence of a glycoprotein (gC) on the virion envelope binds C3b (Friedman et al., *Nature*, 309:633–635 (1984), Kubota et al., *J. Immunology*, 138(4):1137–1142 (1987)). Studies have demonstrated the ability of gCs to regulate complement and protect viruses from complement-mediated neutralization. In group A streptococci, differences in M protein structures and ability to bind fibrinogen and differences in hyaluronate capsule decreased the ability of the streptococcal surface to fix C3. Restriction of C3 deposition resulted in areas resistant to opsonization, whereas other areas on the cell surface remained susceptible (Jacks-Weis et al., *J. Immun.*, 128(4): 1897–902 (1982)). Although these resistant areas did not completely explain the resistance of these bacteria to phagocytosis, it posed the idea that proteins on the surface of organisms could promote evasion of host defenses.

FIG. 10 provides an amino acid sequence (SEQ ID NO:5) corresponding to a 60 kDa±10 kDa C3-binding polypeptide according to this invention. This polypeptide is encoded by the open reading frame of the nucleic acid fragment that has the sequence shown in FIG. 13 (SEQ ID NO:6), i.e., nucleic acids 1–1337. The amino acid sequence of SEQ ID NO:5, SEQ ID NO:5 contains an amino terminus sequence represented by SEQ ID NO:1 and two internal amino acid sequences represented by SEQ ID NO:2 and SEQ ID NO:3.

The amino acid sequences of SEQ ID NOs:1–3 were sufficient to design degenerate oligonucleotide primers represented by SEQ ID NOs:7 and 8. These oligonucleotide primers were used to generate PCR products of up to 1163 base pairs, which are believed to encode at least a portion of GBbcA. The 1163 base pair PCR product was determined not to have nucleic acid identity at the nucleotide level by BLAST sequence analysis to other nucleic acid fragments present in the database. The primers used were:

5'-GAY CAR ACI ACI WSI GTI CAR GT-3' (SEQ ID NO:7), and

5'-CCR TCI GCI III ARI ACY TGR TCR TAR TT-3' (SEQ ID NO:8)

Amplification reactions were performed using genomic DNA of prototypic group B streptococcal strains from nine different group B streptococcal serotypes (see, Example 1) in the polymerase chain reaction using primers derived from the amino acid sequence represented by SEQ ID NO:1 and from the amino acid sequence represented by SEQ ID NO:3, which have a high degree of sequence similarity with portions of GBbcA, to generate degenerate oligonucleotide primers SEQ ID NOs:7 and 8. Prototypic group B streptococcal strains from all nine serotypes showed an 1163 base pair PCR product. This demonstrated that GBbcA is conserved at both the polypeptide level and the nucleic acid level.

In analysis of the translated polypeptide sequence shown in FIG. 10 and represented by SEQ ID NO:5 from the nucleic acid fragment represented by SEQ ID NO:6, a conserved hexapeptide motif LPKTGV (corresponding to amino acids 365–370 represented by SEQ ID NO:5) is a commonly reported region in surface proteins of Gram-positive cocci. It has been proposed that this hexapeptide is responsible for a post-translational modification necessary for the proper anchoring of the polypeptide to the cell wall and indicates that GBbcA is presumably a surface polypeptide utilizing this motif as an anchor region.

The polypeptide of this invention has an apparent molecular weight on a 7.5% SDS-polyacrylamide gel of about 60 kDa (±10 kDa), and preferably has a molecular weight of about 60 kDa to about 70 kDa. An exemplary polypeptide sequence is represented by SEQ ID NO:5. Those of ordinary skill in the art will recognize that some variability in an amino acid sequence is expected and that this variability should not detract from the scope of the invention. For example, conserved mutations do not detract from this invention nor do variations in amino acid sequence.

Accordingly, a polypeptide of the invention has at least 50% amino acid identity, preferably at least 60% amino acid identity, more preferably at least 70% amino acid identity, and most preferably at least 80% amino acid identity to amino acids 1–445 of SEQ ID NO:5 (FIG. 10), and where the polypeptide binds human complement C3, and particularly where the polypeptide is isolated or originally obtained from an *S. agalactiae* bacterium.

Some nucleic acid sequence variability is expected among streptococcal strains and serotypes as is some amino acid sequence variability. Conserved amino acid substitutions are known in the art and include, for example, amino acid substitutions using other members from the same class to which the amino acid belongs. For example, the nonpolar amino acids include alanine, leucine, isoleucine, valine, proline, phenylalanine, and tryptophan. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to affect apparent molecular weight as determined by polyacrylamide gel electrophoresis or isoelectric point. Particularly preferred conservative substitutions include, but are not limited to, Lys for Arg and vice verse to maintain a positive charge; Glu for Asp and vice versa to maintain a negative charge; Ser for Thr so that a free —OH is maintained; and Gln for Asn to maintain a free $NH_2$.

A preferred polypeptide of this invention includes a polypeptide with the amino acid sequence as shown in FIG. 10 and represented by SEQ ID NO:5. Other polypeptides include those binding human complement C3 and having a nucleic acid sequence encoding the polypeptide, wherein the nucleic acid fragment hybridizes to at least a portion of at least one of the nucleic acid fragments represented by SEQ ID NO:6 and/or SEQ ID NO:4 under standard hybridization conditions.

Advantageously, the polypeptide of this invention can be isolated or prepared as a recombinant polypeptide. That is, nucleic acid encoding the polypeptide (e.g., SEQ ID NO:4 or SEQ ID NO:6) or a portion therefrom can be incorporated into a expression vector or incorporated into a chromosome of a cell to express the polypeptide in the cell. The polypeptide can be purified from a bacterium or another cell, such as a eukaryotic cell or an animal cell. Alternatively, the polypeptide can be isolated from a cell expressing the polypeptide, such as a *S. agalactiae* cell.

A method that may be used for obtaining a purified polypeptide from *S. agalactiae* that binds human complement C3 includes the steps of obtaining a polypeptide sample from *S. agalactiae*, precipitating the polypeptide to form a precipitate, applying the precipitate to an affinity column (preferably, a Thiopropyl Sepharose 6B affinity chromatography column comprising methylamine-treated C3), and eluting the C3 binding polypeptide from the column using an elution buffer (preferably including 20% ethanol) (Smith, B., *Characterization of a pneumococcal surface protein which binds complement protein C3 and its role in adhesion,* Univ. of Minnesota, Dissertation, pages 1–77 (1998); Cheng and Hostetter, *American Society for Microbiology 97th General Meeting,* Abstract B-478 (Miami, Fla. (1997)).

A nucleic acid fragment encoding the 60 kDa±10 kDa polypeptide is also part of this invention. A preferred nucleic acid sequence is represented by SEQ ID NO:6. Those of ordinary skill in the art will recognize that some substitution will not alter the C3 binding polypeptide to an extent that the character or nature of the C3 binding polypeptide is substantially altered. For example, nucleic acid fragments with an identity of at least 50% nucleic acid identity, preferably at least 60% nucleic acid identity, more preferably at least 70% nucleic acid identity, and most preferably at least 80% nucleic acid identity to nucleic acids 1–1337 represented by SEQ ID NO:6 is contemplated in this invention. A method for determining whether a particular nucleic acid fragment falls within the scope of this invention is to consider whether or not a particular nucleic acid fragment encodes a polypeptide that binds human complement C3 and has a percent nucleic acid identity of at least 50% nucleic acid identity, preferably at least 60% nucleic acid identity, more preferably at least 70% nucleic acid identity, and most preferably at least 80% nucleic acid identity as compared with the nucleic acid sequence represented by SEQ ID NO:6. Other nucleic acid fragments encoding the C3 binding polypeptide include nucleic acid encoding the polypeptide where the polypeptide has the same amino acid sequence or has at least 50% amino acid identity, preferably at least 60% amino acid identity, more preferably at least 70% amino acid identity, and most preferably at least 80% amino acid identity with the nucleic acid sequence represented by SEQ ID NO:5, but which includes degeneracy with respect to the nucleic acid. A degenerate codon means that a different three letter codon is used to specify the same amino acid. For example, it is well known in the art that the following RNA codons (and therefore, the corresponding DNA codons, with a T substituted for a U) can be used interchangeably to code for each specific amino acid:

| Phenylalanine (Phe or F) | UUU, UUC, UUA or UUG |
| Leucine (Leu or L) | CUU, CUC, CUA or CUG |
| Isoleucine (Ile or I) | AUU, AUC or AUA |
| Methionine (Met or M) | AUG |
| Valine (Val or V) | GUU, GUC, GUA, GUG |
| Serine (Ser or S) | AGU or AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tryptophan (Trp) | UGG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | AGA or AGG |

-continued

| Glycine (Gly or G) | GGU or GGC or GGA or GGG |
| Termination codon | UAA, UAG or UGA |

Further, a particular nucleic acid fragment can be modified to employ the codons preferred for a particular cell type. For example, the preferred codon usage for *E. coli* is known, as are preferred codons for animals including humans. These changes are known to those of ordinary skill in the art and therefore these nucleic acid fragments are considered part of this invention. Other nucleic acid fragments include polynucleotides of at least about 15 nucleotides, and preferably, at least about 30 nucleotides in length as represented by SEQ ID NO:6 where these fragments hybridize to nucleic acid encoding the polypeptides represented by SEQ ID NO: 1, SEQ ID NO:2, and/or SEQ ID NO:3, under standard hybridization conditions.

The nucleic acid fragments of the invention can encode all, none (i.e., fragments that cannot be transcribed, fragments that include regulatory portions of the nucleic acid fragment, or the like) or a portion of the nucleic acid sequence represented by SEQ ID NO:6 and preferably containing a contiguous nucleic acid sequence that encodes at least nine amino acids as represented by SEQ ID NO:5 or SEQ ID NO:2. Because nucleic acid fragments encoding at least a portion of at least one of the nucleic acid fragments represented by SEQ ID NO:6 and/or SEQ ID NO:4 are contemplated in this invention, it will be understood that not all of the nucleic acid fragments will encode a polypeptide with C3 binding activity. Further, the nucleic acid fragment of this invention can be mutated to remove or otherwise inactivate the C3 binding activity of this polypeptide. Therefore, nucleic acid fragments without C3 binding activity that meet the hybridization requirements described above are also contemplated. Methods for mutating or otherwise altering nucleic acid fragments are well described in the art and the production of an immunogenic, but enzymatically inactive polypeptide can be tested for therapeutic and immunogenic utility.

The nucleic acid fragments of this invention can be incorporated into nucleic acid vectors or stably incorporated into host genomes to produce a recombinant polypeptide including recombinant chimeric polypeptide. In one embodiment, the the polypeptide represented by SEQ ID NO:5 is encoded by a nucleic acid fragment in a vector and the vector is in a cell. Preferably, the cell is a prokaryotic cell such as a bacterium. The nucleic acid fragment can exist as the fusion of all or a portion of the nucleic acid fragment with another nucleic acid fragments and the C3 binding polypeptide can exist as a fusion polypeptide of one or more polypeptides where the fusion polypeptide is expressed as a single polypeptide. A variety of nucleic acid vectors of this invention are known in the art and include a number of commercially available expression plasmids or viral vectors.. The use of these vectors is well within the scope of what is ordinary skill in the art.

This invention also relates to antibodies capable of binding (typically specifically binding) to a polypeptide of about 60 kDa±10 kDa, and preferably a polypeptide of about 60 kDa to about 70 kDa, from *S. agalactiae* and preferably where the polypeptide is capable of binding human complement C3. Both monoclonal and polyclonal antibodies can be prepared to a polypeptide according to the invention having a molecular weight of 60 kDa±10 kDa. Preferably, the polypeptide binds human complement C3. Methods for preparing antibodies to a polypeptide are well known and well described, for example, by Harlow et al., (*Antibodies; A Laboratory Manual*. Cold Spring Harbor, N.Y.; Cold Spring Harbor Laboratory Press, 1988). In a preferred example, the antibodies can be human derived, rat derived, mouse derived, goat derived, bovine derived, chicken derived, or rabbit derived. Polypeptide-binding antibody fragments and chimeric fragments are also known and are within the scope of this invention.

The invention also relates to the use of immune stimulating compositions. The term "immune stimulating" or "immune system stimulating" composition refers to a polypeptide composition according to the invention that activates at least one cell type of the immune system in a subject, such as a mammal, preferably a lactating mammal, such as a human, cow, or goat. Preferably, the immune stimulating composition provides an immunizing response or prophylactic benefit in a normal, i.e., uninfected subject, typically a vaccine. However, any measurable immune response obtained by administering an effective amount of the polypeptide is beneficial to the subject in a therapy application or protocol. Preferred activated cells of the immune system include phagocytic cells such as neutrophils or macrophages, T cells, B cells, epithelial cells and endothelial cells. Immune stimulating compositions containing the polypeptides of the invention can be used to produce an antibody in an animal such as a rat, mouse, goat, cow, chicken, rabbit, or a human or an animal model for studying. *S. agalactiae* infection. Preferred immune stimulating compositions include an immune stimulating amount, such as a therapeutically effective amount, of at least one polypeptide as described herein to yield an immune response.

By a "effective amount," as used herein, refers to that amount that is effective for production of a desired result, i.e., immunization and/or therapy. This amount varies depending upon the health and physical condition of a subject's immune system, i.e., to synthesize antibodies, the degree of protection desired, the formulation prepared and other relevant factors. It is expected that the amount will fall in a relatively broad range that can be determined through routine trials.

The term "vaccine" refers to a composition for immunization. This process can include the administration of a polypeptide, antigen, nucleic acid fragment or complementary nucleic acid fragment, e.g., antisense, or antibody, or suspensions thereof, wherein upon administration, active immunity and protection are provided against *S. agalactiae* colonization and/or infection. Typically, such vaccines are prepared as injectables, either as liquid solutions or suspensions. Solid forms suitable for solution in, or suspension in, liquid prior to injection may also be prepared. The vaccine preparation may optionally be emulsified, or encapsulated in liposomes.

The immune stimulating composition (such as a vaccine) can further include other polypeptides in a pharmaceutically acceptable buffer or carrier, such as PBS (phosphate buffer saline) or another buffer recognized in the art as suitable and safe for introduction of polypeptides into a host to stimulate the immune system. The immune stimulating compositions can also include polypeptides that can be used as components of vaccines, as conjugates coupled to capsular polysaccharide which act as adjuvants to boost an immune response, i.e., antibody response, or as whole polypeptide vaccine candidates themselves, in addition to other immune system stimulating polypeptides such as adjuvants or immune stimulating polypeptides, from *S. agalactiae* or other organisms. For example, a cocktail of polypeptides may be most useful for controlling *S. agalactiae* infection.

Preferably one or more fragments of the polypeptides of this invention are used in a vaccine preparation to protect against or limit *S. agalactiae* colonization or the pathogenic consequences of *S. agalactiae* colonization and infection, i.e., invasive disease.

The active immune stimulating ingredients are often mixed with excipients or diluents that are pharmaceutically acceptable as carriers and compatible with the active ingredient. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof In addition, if desired, the immune stimulating composition (including vaccine) may contain minor amounts of auxiliary substances such as wetting or emulsifying agents, pH buffering agents, and/or adjuvants which enhance the effectiveness of the immune stimulating composition.

Examples of adjuvants or carriers that may be effective include but are not limited to: aluminum hydroxide, N-acetyl-muramyl-L-threonyl-D-isoglutamine (thr-MDP); N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2' dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween 80 emulsion.

This invention also relates to a method for inhibiting *Streptococcus agalactiae*-mediated C3 binding by contacting an *S. agalactiae* bacterium with a polypeptide, such as an antibody or another polypeptide that is capable of binding to an isolated polypeptide of about 60 kDa±10 kDa from *Streptococcus agalactiae*. The polypeptide capable of binding to an isolated polypeptide of about 60 kDa±10 kDa can be an antibody or a fragment thereof or the polypeptide can be a chimeric polypeptide that includes the antibody binding domain, such as a variable domain, from antibody that is capable of specifically recognizing an isolated polypeptide of about 60 kDa±10 kDa from *Streptococcus agalactiae* having C3 binding activity.

The isolated *S. agalactiae* polypeptide of this invention can be isolated, and optionally purified, and the isolated polypeptide thereof can be used to produce an immunologic response, including, in one example, an antibody response in a human, cow, goat or other experimental animal. Polypeptides without C3 binding ability can be tested for their ability to limit the effects of *S. agalactiae* colonization and infection. Similarly, the polypeptide of this invention can be modified, such as through mutation, to interrupt or inactivate the C3 binding activity of the polypeptide. Antibodies that inhibit the C3 binding activity of the polypeptide of this invention may be used as a strategy for preventing C3 binding and for promoting clearance of *S. agalactiae* through the opsonic pathway.

An isolated polypeptide can be used in assays to detect antibody to *S. agalactiae* or as part of a vaccine or a multi-valent or multiple polypeptide containing vaccine for *S. agalactiae* therapy. Polypeptides used as components of vaccines, as antigenic conjugate molecules coupled to a capsular polysaccharide which act as adjuvants to boost an immune response, i.e., antibody response, or as whole polypeptide vaccine candidates themselves are also included. A typical antigenic conjugate molecule may contain a capsular polysaccharide derived from Group B Streptococcus and a polypeptide according to the invention wherein two or more side chains terminating in sialic acid residues of the capsular polysaccharide component are each linked through a secondary amine bond to the polypeptide. Preferably, the antigenic conjugate molecule is administered in an effect amount to a mammal, such as a lactating mammal (e.g., human, cow, goat, etc.) at risk for being colonized or infected by Group B Streptococcus.

The term "treat" or "treatment," as used herein, refers to prophylaxis, i.e., immunization, and/or therapy of either normal mammalian subjects, preferably lactating mammalian subjects such as humans, cows, goats, etc., or mammalian subjects colonized with, diagnosed with, or exhibiting characteristics or symptoms of various *S. agalactiae* infections. The term "therapy" refers to providing an effect amount of a polypeptide according to the invention to a mammalian subject such that the subject exhibits few or no symptoms of a streptococcal colonization or infection. Such treatment can be accomplished by administration of nucleic acid fragments (sense or antisense), polypeptides, or antibodies of the instant invention.

Another specific aspect of the present invention relates to using a vector (e.g., a vaccine vector) expressing an isolated polypeptide. Accordingly, in a further aspect this invention includes a method of inducing an immune response in a mammal, that includes providing to a mammal a vector expressing at least one, or a mixture of an isolated polypeptide of the invention. The polypeptides of the present invention can be delivered to the mammal using a live vector, in particular using live recombinant bacteria, viruses or other live agents, containing the genetic material necessary for the expression of the polypeptide or polypeptides as a foreign polypeptide. Particularly, bacteria that colonizes the gastrointestinal tract, such as Salmonella, Shigella, Yersinia, Vibrio, Escherichia and BCG have been developed as vectors, and these and other examples are discussed by J. Holmgren et al., *Immunobiol.*, 184, 157–179 (1992) and J. McGhee et al., *Vaccine*, 10, 75–88 (1992).

An additional embodiment of the present invention relates to a method of inducing an immune response in a mammalian subject, preferably a lactating mammalian subject, including administering to the subject an amount of a nucleic acid fragment encoding an isolated polypeptide of this invention, optionally with a transfection-facilitating agent, where the polypeptide retains immunogenicity and, when incorporated into an immune stimulating composition, e.g., vaccine, and administered to a human, goat, or cow, provides protection without inducing enhanced disease upon subsequent infection of the human with *S. agalactiae* pathogen. Transfection-facilitating agents are known in the art.

It is further contemplated that the antisense strand of the nucleic acid fragment represented by SEQ ID NO:4 and/or SEQ ID NO:6 encoding the 60 kDa±10 kDa polypeptide represented by SEQ ID NO:5, may be used as a vaccine or as a treatment for streptococcal colonization or infection. An "antisense" nucleic acid fragment is defined as a non-coding nucleic acid that is complementary, i.e., a complementary nucleic acid strand, to all or a portion of the nucleic acid fragment represented by SEQ ID NO:6. For example, the antisense nucleic acid fragment for 5'-ATGTCAAGC-3' is 3'-TACAGTTCG-5'. Delivery of antisense nucleic acid or oligonucleotides into a mammal may result in the production of antibody by the mammal or in the incorporation of the nucleic acid fragment into living bacteria or other cells whereby transcription and/or translation of all or a portion of the 60 kDa±10 kDa product is inhibited.

Introduction of an antisense nucleic acid fragment can be accomplished, for example, by loading the antisense nucleic acid fragment into a suitable carrier, such as a liposome, for introduction into streptococci or infected cells. Typically, an antisense nucleic acid fragment having eight or more nucleotides is capable of binding to the bacterial nucleic acid or bacterial messenger RNA. The antisense nucleic acid fragment typically contains at least about 15 nucleotides, preferably at least about 30 nucleotides or more nucleotides to provide necessary stability of a hybridization product of bacterial nucleic acid or bacterial messenger RNA. Introduction of these nucleic acids preferably inhibits the transcription or translation of at least one endogenous *S. agalactiae* nucleic acid fragment. Methods for loading antisense nucleic acid are known in the art.

The present invention also provides nucleic acid fragment having an open reading frame of 1337 base pairs represented by SEQ ID NO:6, that encodes a polypeptide that has a molecular weight of about 60 kDa±10 kDa represented by SEQ ID NO:5. The 60 kDa±10 kDa polypeptide, described herein, is further characterized as a human complement C3 binding polypeptide.

In another aspect of the invention, the nucleic acid fragment and polypeptide can be employed as a diagnostic tool, either as an immunological detection of GBS in carriers, colonized humans or other mammals, such as lactating mammals, by detection of GBS antigen, or by a molecular based rapid diagnostic tool for colonization or infection utilizing hybridization of gbbcA nucleic acid.

All references and publications cited herein are expressly incorporated by reference into this disclosure. There are a variety of alternative techniques and procedures available to those of skill in the art which would similarly permit one to successfully perform the intended invention in view of the present disclosure. It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

EXAMPLES

Materials

Protein A, methylamine, EDTA, bovine serum albumin (BSA), lysozyme, mutanolysin, Tween 20, N-lauroylsarcosine, sodium citrate, glycine, bromophenol blue, maleic acid, phenol:chloroform:isoamyl, trypsin, NaH$_2$PO$_4$, Na$_2$HPO$_4$ (Sigma, St. Louis, Mo.).

Proteinase K, glycerol (Gibco BRL, Life Technologies, Grand Island, N.Y.).

Tris, Tris HCl (Research Organics, Cleveland, Ohio).

SDS, β-mercaptoethanol, BIS-acrylamide; polyvinylidene difluoride (PVDF) membrane, nitrocellulose membrane (Bio-Rad, Hercules, Calif. ).

NaCl, ethanol, methanol, trichloracetic acid (TCA), Na$_2$HPO$_4$, KH$_2$PO$_4$ (Fisher, Itasca, Ill.).

Chloroform, NaOH (Mallinckrodt Baker, Inc., Paris, Ky.).

Example 1

Bacterial Strains, Media and Growth Conditions

A variety of *Streptococcus agalactiae* strains were available and serotyped in our laboratory. Strains representing various serotypes were as follows: type Ia/c (MN-110), type Ia/R4 (S2-00573), type II/R4 (MSP 1A-00062), type III/R4

(76-043), type IV/R4 (P8-00619R), type V/R1/R4 (MN-106), and NT/R3/R4/R5 (Compton 25/60 83–545).

The following prototypic strains were used in PCR and Southern blot studies: Ia (wild type; S3-3630P), Ib (H36B; 71–733), Ia/c (A909; 71–736), II (18RS21/19/2; 71–734), m (wild type; Boston M781), IV (Rabinowitz 3139; 81–305), V (Prague SS-169; 87–601), VI (Prague SS-1214; 92–085), VII (Prague 7271; 87–603), VIII (JM9-130013; JM9). (All strains were from the Group B Streptococcus Molecular Reference Laboratory at the University of Minnesota, Dr. Patricia Ferrieri).

*Escherichia coli* strains XL1-Blue MRF', SOLR, and ExAssist were all strains supplied by Stratagene (La Jolla, Calif.), with the. custom made library in the Lambda Zap II vector and were used according to manufacturer's protocols ( Stratagene).

Human Antisera Used

Maternal/infant paired antisera were collected by standard procedure from colonized mothers and neonates and stored at −80° C. until use: 148/149, 2516/2517. Neonatal antisera were collected from cord blood of neonates later determined to be colonized with GBS (from epidemiological studies of pregnant women colonized with GBS; samples were removed at the time of delivery from the placenta). Adult antisera included antisera from colonized mothers, antiserum from adult RP, PF antiserum previously identified as lacking antibodies to other GBS proteins, BS IgG antiserum as normal human control, and BS IgG-, an antiserum deficient in IgG after passage over a protein A column, with BS IgG eluate containing recovered IgG after elution.

Bacterial Growth

*S. agalactiae* strains were grown to late exponential or stationary phase in Todd-Hewitt Broth (THB) (Fisher, Pittsburgh, Pa.) at 37° C. without shaking, aliquoted for stock cultures, and stored at −80° C. until use. For each experiment, 50 μl thawed aliquot stock bacteria were inoculated into 10 mls of fresh THB and grown to stationary phase (THB $OD_{600}$~0.5–0.7).

Preparation of C3

Human complement protein C3 used in these experiments was a commercially purified product (Cal Biochem, La Jolla, Calif.) stored at −80° C. Prior to use, C3 was thawed on ice and treated with 0.1 M methylamine ($CH_3NH_2$ in 0.1 M Tris/0.01 M EDTA, pH 8.0) for 90 minutes at 37° C. C3 was then dialyzed overnight at 4° C. in phosphate buffered saline (PBS) (1 volume C3 in 1000 volumes PBS). C3 was subsequently electrophoresed on a 7.5% sodium dodecyl sulfate polyacrylamide gel (SDS-PAGE) under reducing conditions and exhibited the typical two-chain pattern with the α-chain migrating at about 115 kDa and the β-chain migrating at about 75 kDa.

Example 2

Identification of GBbcA, in Streptococcal Supernatants and Trypsinized Cell Extracts GBS strains were grown to mid-late exponential phase, centrifuged, and the supernatant containing secreted proteins was precipitated with a final concentration of 10% trichloroacetic acid (TCA) at 4° C. overnight. For extraction of surface proteins with trypsin, cells were washed in Sorensen's Phosphate Buffer (0.06M $Na_2HPO_4$, 2 mM $KH_2PO_4$, pH 8.2) then treated with 0.1% trypsin in Sorensen's Phosphate Buffer for 30 minutes at 37° C. The reaction was stopped at pH 6 on ice for 5 minutes. GBS secreted proteins were then electrophoresed on 7.5% SDS-PAGE under reducing conditions (100 mM Tris (pH 6.8), 10% glycerol, 0.005% bromophenol blue, 2% SDS and 5% β-mercaptoethanol loading buffer), and transferred using transfer buffer (25 millimolar (mM) Tris, 192 mM Glycine, 0.1% SDS, and 20% Methanol) for 1.5 hours at 200 volts to nitrocellulose membranes for Western blot analysis (25 millimolar (mM) Tris, 192 mM Glycine, 0.1% SDS, and 20% Methanol).

For Western Blot, nitrocellulose membranes of GBS secreted proteins and GBS extracts were blocked for 1 hour with 5% nonfat dry milk (Carnation, Nestle USA, Inc., Solon, Ohio) in 1×ECL-TTBS (2 mM Tris, 17.3 mM NaCl, 0.1% Tween 20) at 23° C., washed 3 times at 23° C. with 1×ECL-TTBS, and incubated with purified methylamine treated human C3 (50 nanograms/milliliter (ng/ml) in 3×ECL-TTBS, 3% bovine serum albumin (BSA)) 1 hour at 23° C. on a rocker. After washing 3 times with 1×ECL-TTBS, bound C3 was detected using horseradish peroxidase (HRP)-conjugated goat anti-human C3 (at 1:2000) (ICN Cappel, Costa Mesa, Calif.). The blots were washed and developed using the SUPERSIGNAL system (Pierce, Rockford, Ill.). Alternately, blots were incubated with biotinylated C3 prepared by incubation of C3 with Biotin, Sulfo-NH-LC (Pierce, Rockford, Ill.) per manufacturer's directions; and detected with HRP-avidin (ICN Cappel, Costa Mesa, Calif.).

Example 3

Purification of GBbcA Protein on C3 Column

In a method reported by Smith, B., *Characterization of a pneumococcal surface protein which binds complement protein C3 and its role in adhesion,* Univ. of Minnesota, Dissertation, pages 26–27 (1998), 4 mg of methylamine treated C3 was immobilized to a Thiopropyl Sepharose 6B column matrix (Pharmacia, Piscataway, N.J.) as per manufacturer's instructions. All molecules of C3 attached via the sulfhydryl residue exposed by methylamine disruption of the C3 thiolester. 3.5 liters (L) of GBS 76-043 supernatant was precipitated with a final concentration of 10% TCA. Precipitate was resuspended in 0.1M Tris to pH 7.0 and passed over the methylamine treated C3 column.

The column was subsequently washed with 50 mls of 0.1 M Tris-HCl and 0.5 M NaCl, pH 7.0. One ml fractions were eluted from the column with 20% ethanol in Tris-HCl/NaCl. 30 μl of each fraction were then electrophoresed on a 7.5% SDS-PAGE under reducing and non-reducing conditions. A band having a molecular weight of about 60 kDa±10 kDa was visualized by silver stain (Research Organics, Cleveland, Ohio).

Example 4

Detection of Maternal and Neonatal Human Antibodies to GBbcA in Western Blot

After electrophoresis of purified GBbcA on a 7.5% SDS-PAGE, a Western blot was performed as described above. Nitrocellulose membranes containing the transferred protein were blocked, washed, and incubated for 1 hour at 23° C. on a rocker with either maternal antisera, neonatal antisera, or other human control subject antisera, including BS IgG-antiserum rendered IgG deficient by passage over a protein A column, and IgQ eluate antiserum containing recovered IgG antibodies after elution, all at 1:100 or with purified methylamine treated human C3 (50 ng/ml) as a control for comparison.

After washing 3 times with 1×ECL-TTBS, bound antibodies specific for GBbcA were detected using HRP-goat anti-human. IgG affinity purified antisera (1:1000) (ICN Cappel, Costa Mesa, Calif.), or bound C3 was detected using HRP-conjugated goat anti-human C3 as described above. The blots were washed and developed using the SUPERSIGNAL system per manufacturer's instructions (Pierce, Rockford, Ill.).

Example 5

Determination of GBbcA Amino Acid Sequence

Approximately 80 picomoles of purified GBbcA protein were immobilized on polyvinylidene difluoride (PVDF) membrane or maintained in a 7.5% SDS-PAGE gel slices and subjected to amino-terminal and internal peptide sequencing at Harvard Microchemistry Facility, Cambridge, Mass.

Example 6

Generation of GBbcA Sequence by Polymerase Chain Reaction

From amino acid sequences determined above, 2 µM degenerate oligonucleotides were derived from the amino acid sequences represented by SEQ ID NO:1 (FIG. 7) and SEQ ID NO:3 (FIG. 12), which have a high degree of sequence similarity with portions of GBbcA (SEQ ID NO:5), and used as primers to amplify 75 ng of 76-043 genomic DNA by Polymerase Chain Reaction with the addition of dNTP's (Applied Biosystems, Inc., Foster City, Calif.), buffer, $MgCl_2$ (Promega, Madison, Wis.), and Taq polymerase (Promega, Madison, Wis.). The amplified product of 1163 base pairs (FIG. 8) was cleaned by WIZARD PCR Preps DNA, Purification System (Promega, Madison, Wis.), and was sequenced by the University of Minnesota Microchemical Facility. A digoxygenin-probe was generated by the addition of digoxygenin-11-dUTP (alkali labile) per manufacturer's instructions (Roche Molecular Biochemicals, Indianapolis, Ind.) using degenerate primers SEQ ID NOs:7 and 8. Probe concentration was assayed by dot blot and determined to be 100 ng/ul such that the digoxygenin-labeled probe was used at a final concentration in hybridization buffer at 1000 ng/ml to screen the library and for Southern blot.

Example 7

Preparation of Genomic DNA

Genomic DNA for PCR template DNA and for construction of the genomic library was isolated from all GBS strains using an adapted method previously described (Suvorov et al., Infect. and Immun., 65(1):191–196 (1997)). GBS strains were grown overnight to stationary phase in 10 mls THB, 200 µl 0.5M EDTA was subsequently added on ice, and cells were centrifuged, washed in 1 ml special STE (50 mM Tris-Cl, 1 mM EDTA, 0.1M NaCl, pH 8.0), and resuspended in 100 ul of STE (10 mM Tris-Cl, 1 mM EDTA, 0.1M NaCl, pH 8.0). 2.5 µl of lysozyme (10 mg/ml), 11 µl mutanolysin (1 mg/ml), and 20 µl proteinase K (20 mg/ml) were added, and cells were incubated 55° C. for 30 minutes. SDS was added at a final concentration of 1% and cells were incubated at 55° C. for an additional 30 minutes. Cells were centrifuged to remove cellular debris and phenol:chloroform extracted to purify DNA.

Example 8

Construction and Screening of GBS Genomic Library

A genomic library of EcoRI digested 76-043 DNA in Lambda ZapII vector was created by Stratagene (Stratagene, LaJolla, Calif.). A digoxygenin-labeled probe was generated by the addition of digoxygenin-11-dUTP prior to polymerase chain reaction per manufacturer's instructions (Roche Molecular Biochemicals, Indianapolis, Ind.) 1163 PCR fragment was used to screen replica filters of about 11,500 plaques from the library after incubation with XL1-Blue MRF' bacterial host strain (Stratagene) and plated on NZCYM bottom agar (Life Technologies, Grand Island, N.Y.) in 0.7% top agarose (ultra pure, Gibco BRL Life Technologies, Grand Island, N.Y.).

After denaturation (0.5N NaOH, 1.5M NaCl) and neutralization (1.5M NaCl, 1M Tris-HCl, at pH 7.5) of nylon filters (Roche Molecular Biochemicals, Indianapolis, Ind.), plaques were lysed and DNA bound to filters by baking at 80° C. for 2 hours prior to prehybridization for 1 hour at 62° C. in Standard hybridization solution (5×SSC, 0.02% SDS, 0.1% N-lauroylsarcosine, 1% Blocking Reagent (Roche Molecular Biochemicals, Indianapolis, Ind.)) and hybridization with the 1337 bp gbbcA digoxygenin probe (1000 ng/ml) in Standard hybridization solution overnight at 62° C. Stringency washes twice with 2×SSC, 0.1% SDS for 5 minutes and once with 0.5×SSC, 0.1% SDS for 15 minutes at 62° C. were followed by digoxygenin detection protocol per manufacturer's instructions (Roche Molecular Biochemicals, Indianapolis, Ind.) on BioMax MR film (Fisher, Itasca, Ill.).

Plaques identified in the initial screening were re-hybridized with the 1163 PCR fragment probe in a secondary screen. Plaques with the strongest signal were chosen for in vivo excision of the pBluescript SK(−) phagemid by co-infection with helper phage according to procedure provided by Stratagene.

After in vivo excised clones were identified using the 1183 bp digoxygenin probe, plasmids were prepared using Promega WIZARD miniprep DNA purification system and were sequenced at the University of Minnesota Advanced Genetic Analysis Center. The currently identified 1337 bases (SEQ ID NO:6) presumably is a portion of the gene encoding the Group B Streptococcus binds complement C3,protein, GBbcA. Further sequences will be added until a termination codon is determined.

Example 9

Preparation of Anti-GBbcA Antibodies

Pooled fractions of purified GBbeA were precipitated in 95% ethanol overnight, resuspended in 100 mM Tris (pH 6.8), 10% glycerol, 0.005% bromophenol blue, 2% SDS and 5% β-mercaptoethanol loading buffer and electrophoresed on a 7.5% SDS-PAGE. Purified GBbcA was excised from the gel and sent to Cocalico Biologicals, Inc., Reamstown, Pa. Pre-bleed sera and test bleed rabbit antisera (1:5) were tested by. Western blot for detection of GBbcA. GBbcA protein was electrophoresed on 7.5% SDS-PAGE. Nitrocellulose membranes were incubated with antisera from rabbit umn62, and antibody binding was detected with HRP-conjugated goat anti-rabbit (affinity purified) secondary antibody. Antibodies present in post immunization test bleed antisera bound GBbcA protein, whereas prebleed antisera did not bind.

Results

Surface Expression, Secretion and Identification of GBbcA

The polypeptide GBbcA was identified by binding commercially available purified human complement C3 protein in Western blot, and detection with HRP-conjugated goat anti-human C3 antibodies. The polypeptide also bound biotinylated C3 with detection by HRP-conjugated avidin.

FIG. 1 shows a type III invasive strain 76-043 that was grown in Todd-Hewitt broth to late exponential or stationary phase cultures and subsequently centrifuged. Cells were trypsinized to remove surface polypeptides and supernatants were precipitated to collect secreted polypeptides. Surface expressed and secreted polypeptides were electrophoresed on a 7.5% SDS-PAGE and transferred to nitrocellulose membrane. Surface expressed and secreted polypeptides of approximate molecular weights 60 kDa±10 kDa bound commercially available purified human C3 and were detected with HRP-conjugated goat anti-human C3. Thus, a novel polypeptide was identified that bound complement protein C3.

Conservation of GBbcA Polypeptide in Many Group B Streptococcal Serotypes

Figure 2:
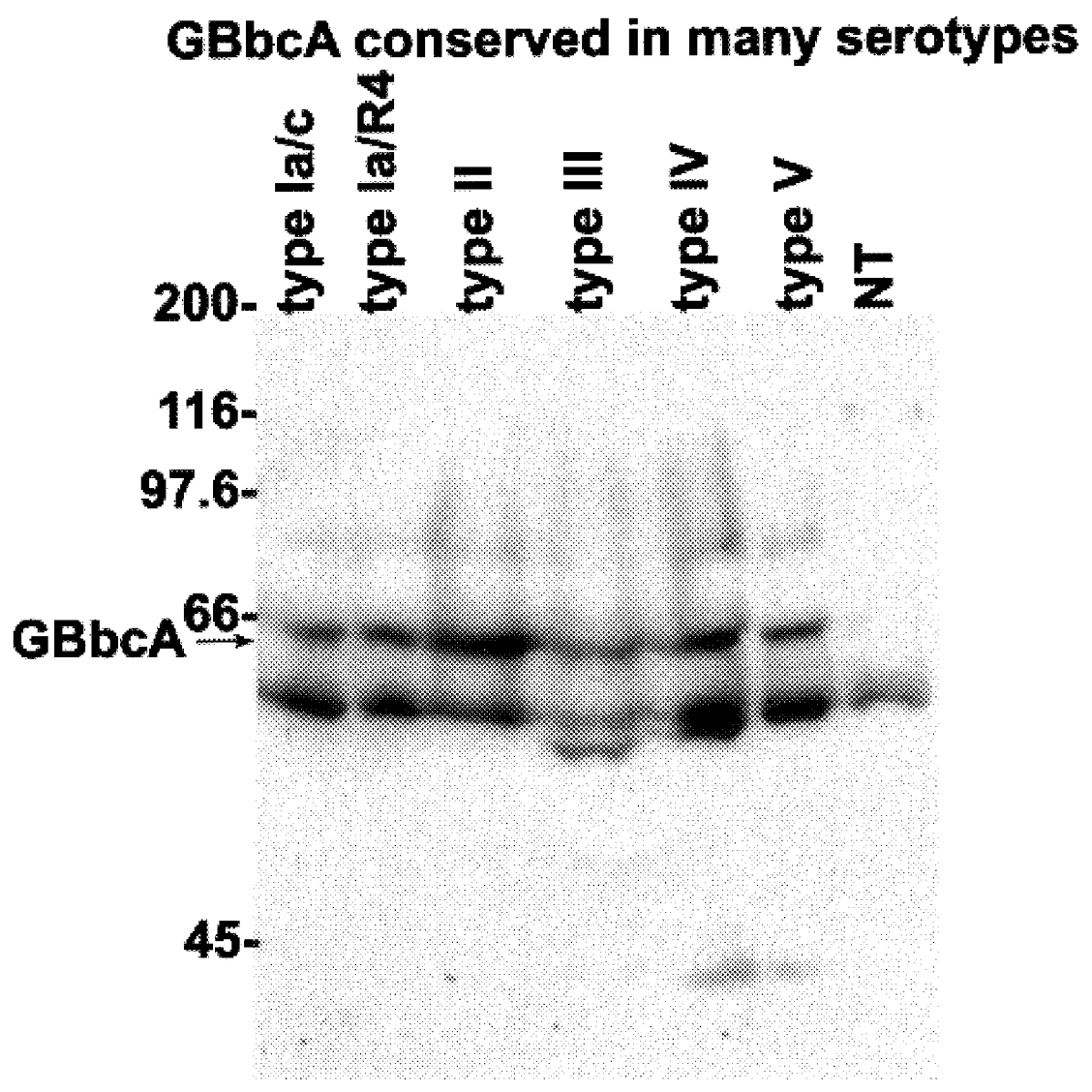

FIG. 2 shows representative strains from group B streptococcal serotypes I, II, II, IV, V, and NT that were grown to late exponential/stationary phase. Western blots detected one or more C3 binding polypeptides (60 kDa±10 kDa) using human C3 and HRP-goat anti-human C3 antibodies or biotinylated C3 and HRP-avidin. Whether the detection of lower bands by Western blot indicates degradation of the 60 kDa±10 kDa C3 binding polypeptide, GBbcA, or indicates the identification of additional binding polypeptides, is yet to be determined. Regardless, conservation of the 60 kDa±10 kDa C3 binding polypeptide, GBbcA, in GBS serotypes I, II, HI, IV and V, has been demonstrated and is significant in that many of these serotypes are associated with invasive disease.

Conservation of the gbbcA Nucleic Acid Shown by PCR

Figure 9:
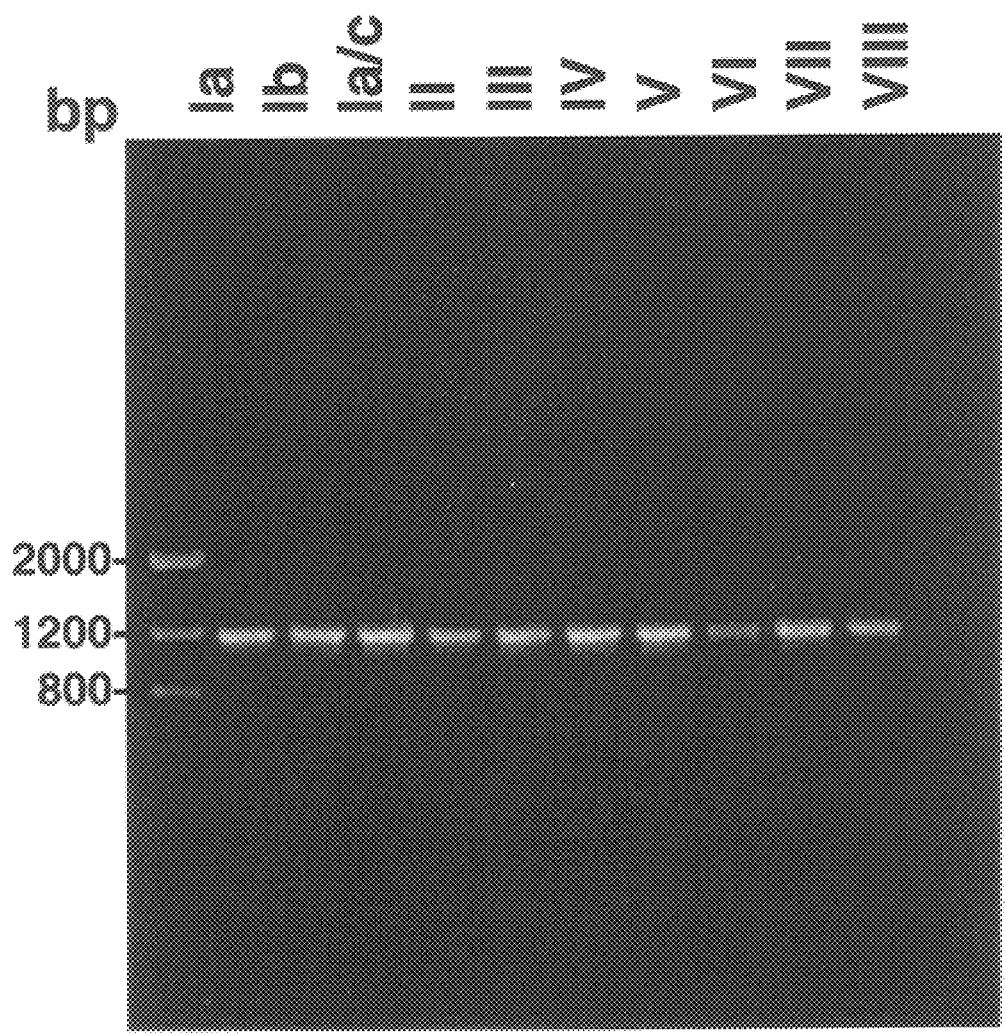

FIG. 9 shows conservation of gbbcA nucleic acid by polymerase chain reaction of prototypic strains from all nine serotypes Ia, Ib, Ia/c, II, III, IV, V, VI, VII, and VIII. 75 ng genomic DNA from prototypic strains was added to 2 mM degenerate oligonucleotides (SEQ ID NO:7 and SEQ ID NO:8) with the addition of dNTPs (Applied Biosystems, Inc., Foster City, Calif.), buffer, MgCl$_2$, Taq polymerase (Promega, Madison, Wis.) and was subjected to Polymerase Chain Reaction. The amplified product containing approximately 1163 base pairs was conserved in all serotypes.

Purification of GBbcA

The C3 binding polypeptide GBbcA has been purified from a type III invasive strain, 76-043, which has been previously well characterized in our laboratory with respect to serotype, polypeptide profiles, virulence in animal studies in animal models of infection, and identification with antisera in our laboratory. GBbcA was identified from its cell associated or secreted form, and was purified as a secreted polypeptide from TCA precipitated supernatants on a C3 affinity column.

FIG. 3 shows TCA precipitated supernatants that were passed over the C3 column and GBbcA bound. After the column was washed, purified GBbcA was eluted with 20% ethanol in column buffer. Elution fractions were collected and polypeptides silver stained after electrophoresis on 7.5% SDS-PAGE. The corresponding Western demonstrated that purified GBbcA at 60 kDa±10 kDa was eluted and bound C3 as did lower bands which could represent degradation products or separate polypeptides.

Immunogenicity of GBbcA is Suggested

Purified GBbcA was sent to Cocalico for antibody production in a rabbit. Antiserum umn62 received from Cocalico 56 days post inoculation, detected a polypeptide at 60 kDa±10 kDa and a lower polypeptide at 55 kDa±10 kDa at a titer of 1:5 on Western blot, which could signify that the one is a degradative product of the other. Prebleed rabbit antiserum did not detect GBbcA.

FIG. 4 demonstrates immunogenicity of GBbcA using rabbit umn62 antiserum and HRP-goat anti-rabbit antibodies.

Figure 6:
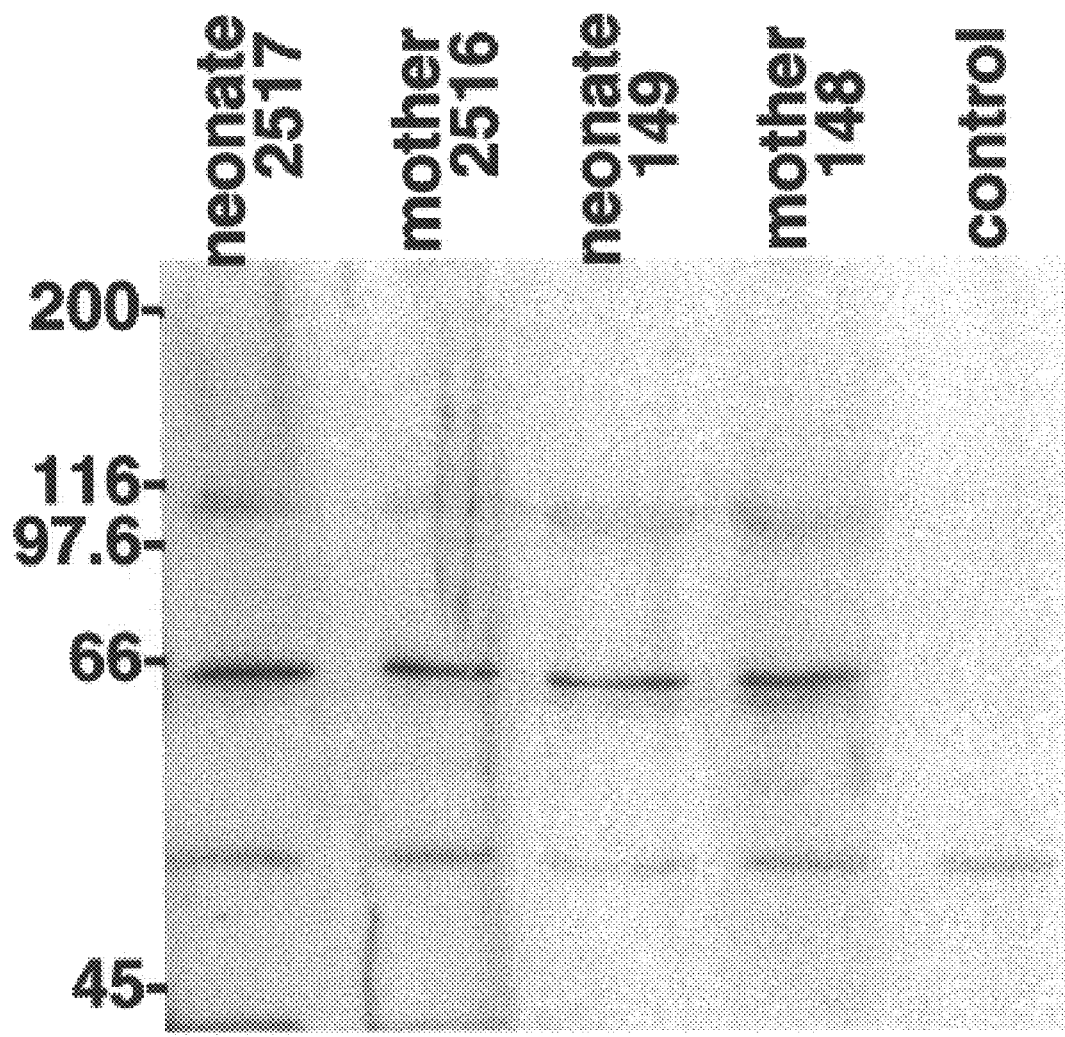

In addition in FIG. 5, immunogenicity was suggested using human antiserum from adults and colonized mothers, and cross placental transfer of antibodies was suggested using human serum from cord blood of colonized neonates (FIG. 6). TCA precipitated supernatants of 76-043 or purified GBbcA were electrophoresed on SDS-PAGE. Mother/neonate pairs of antisera (1:1000) detected GBbcA at 60 kDa and a lower band of a smaller polypeptide. Antiserum passed over a protein A column and depleted of IgG acted as a negative control and did not detect GBbcA at 1:1000 whereas IgG recovered from the eluate detected GBbcA at 1:1000.

The presence of antibodies that recognize GBbcA suggests that group B Streptococcus colonized mothers produced antibodies to GBbcA and to the smaller polypeptides as well. Passive placental transfer of maternal antibodies was suggested by the presence of antibodies that recognize GBbcA from neonatal cord.

Characterization of the Gene Encoding GBbcA

Purified GBbcA was sent to Harvard Microchemical Facility for N-terminal and internal amino acid sequencing. We obtained sequence data for an internal peptide: peak 27 (SEQ ID NO:2) which is 12 amino acids, and for amino acid sequences represented by SEQ ID NO:1 and SEQ ID NO:3 (peak 79). These amino acid sequences were sufficient to design degenerate oligonucleotide primers (SEQ ID NOs:7 and 8) which were used to generate an 1163 base pair PCR product (FIG. 8), which presumably encode GBbcA and do not have similarity at the nucleotide level by BLAST sequence analysis to others in the database.(FIG. 8). Further conservation at the molecular level was demonstrated by polymerase chain reaction. In FIG. 9, genomic DNA of prototypic group B streptococcal strains from all nine group B streptococcal serotypes was used in the polymerase chain reaction using degenerate primers SEQ ID NO:7 and SEQ ID NO:8 generated from amino acid sequences SEQ ID NO:1 and SEQ ID NO:3 (peak 79), respectively. Prototypic group B streptococcal strains for all nine serotypes demonstrated an 1163 base pair PCR product (FIG. 8). This demonstrated that GBbcA is conserved not only at the polypeptide level but also that conservation of nucleic acid is evident.

To identify the nucleic acid of gbbcA, a genomic library was created in the lambda ZapII vector system by Stratagene. The library was screened using the 1163 base pair digoxygenin-labeled PCR product. The PCR product used as a probe is shown in FIG. 8. The gbbcA nucleic acid fragment is shown in FIG. 13 and is represented by SEQ ID NO:6.

What is claimed is:

1. An isolated nucleic acid fragment that hybridizes to at least a portion of at least one of the nucleic acid fragments represented by SEQ ID NO:6 or SEQ ID NO:4 or their complementary strands under hybridization conditions of prehybridization for 1 hour at 62° C. in hybridization solution (5×SSC (1×SSC is 0.15 M NaCL, 0.015 M sodium citrate), 0.02% sodium dodecyl sulfate (SDS), 0.1% N-lauroylsarcosine, 1% Blocking Reagent) followed by two stringency washes with 2×SSC, 0.1% SDS for 5 minutes at room temperature and once with 0.5×SSC, 0.1% SDS for 15 minutes at 62° C., said isolated nucleic acid fragment encodes a polypeptide that binds human complement C3 protein.

2. The nucleic acid fragment of claim 1 isolated from *S. agalactiae*.

3. The nucleic acid fragment of claim 1 which encodes a polypeptide represented by. SEQ ID NO:5.

4. The nucleic acid fragment of claim 1 in a nucleic acid vector.

5. The nucleic acid fragment of claim 4 wherein the nucleic acid vector is an expression vector capable of producing a polypeptide.

6. An isolated nucleic acid having at least 50% nucleic acid identity to the nucleic acid fragments represented by SEQ ID NO:6 or SEQ ID NO:4, and which hybridizes under hybridization conditions of prehybridization for 1 hour at 62° C. in hybridization solution (5×SSC (1×SSC is 0.15 M NaCL, 0.015 M sodium citrate), 0.02% sodium dodecyl sulfate (SDS), 0.1% N-lauroylsarcosine, 1% Blocking Reagent) followed by two stringency washes with 2×SSC, 0.1% SDS for 5 minutes at room temperature and once with 0.5×SSC, 0.1% SDS for 15 minutes at 62° C., to at least a portion of at least one of the nucleic acid fragments represented by SEQ ID NO:6 or SEQ ID NO:4 or their complementary strands, said nucleic acid encoding a polypeptide that binds human complement C3 protein.

7. An isolated polynucleotide encoding a polypeptide comprising the amino acids represented by SEQ ID NO:5.

8. The polynucleotide of claim 7 wherein the polypeptide binds human complement C3.

9. An isolated host cell comprising a nucleic acid fragment of claim 1.

10. The cell of claim 9 wherein the cell is a bacterium or a eukaryotic cell.

11. An isolated nucleic acid fragment comprising SEQ ID NO:6 or SEQ ID NO:4 or their complementary strands.

12. An isolated RNA transcribed from a double-stranded nucleic acid comprising a nucleic acid fragment of claim 2.

13. An isolated nucleic acid fragment encoding a polypeptide having at least 50% amino acid identity to SEQ ID NO:5, said polypeptide binds to human complement C3 protein.

14. An isolated nucleic acid fragment encoding a polypeptide having at least 60% amino acid identity to SEQ ID NO:5, said polypeptide binds to human complement C3 protein.

15. An isolated nucleic acid fragment encoding a polypeptide having at least 70% amino acid identity to SEQ ID NO:5, said polypeptide binds to human complement C3 protein.

16. An isolated nucleic acid fragment encoding a polypeptide having at least 80% amino acid identity to SEQ ID NO:5, said polypeptide binds to human complement C3 protein.

17. An isolated nucleic acid fragment consisting essentially of at least 30 nucleotides of SEQ ID NO:4, wherein said nucleic acid fragment encodes a polypeptide that binds to human complement C3 protein.

* * * * *

UNITED STATES PATENT AND TRADEMARK OFFICE
CERTIFICATE OF CORRECTION

PATENT NO. : 6,582,950 B1
DATED : June 24, 2003
INVENTOR(S) : Smith et al.

It is certified that error appears in the above-identified patent and that said Letters Patent is hereby corrected as shown below:

Column 1,
Line 31, delete "GBS,." and insert -- GBS. --
Between lines 47 and 48, insert paragraph
-- Surface polypeptides of *S. agalactiae* have been under investigation for several years (Lancefield and Perlman, *J. Exp. Medicine*, 96:83-97 (1952)). First termed surface antigens, Lancefield and Perlman first identified C and R antigens. Wilkinson and other investigators subsequently identified an array of other antigens (Wilkinson, *Infection and Immunity*, 4(5):596-604 (1971)). To date, in group B *Streptococcus*, many surface polypeptides have been grouped phenotypically. Some of these polypeptides have been characterized at the molecular level, and some have been studied with respect to biological function. --

Column 3,
Line 41, delete "streptococcalstrains" and insert -- streptococcal strains --

Column 7,
Line 47, delete "V1H" and insert -- VIII --
Line 53, delete "60. kDa±10" and insert -- 60kDa±10 --
Line 67, after "electrophoresis" delete ","

Column 8,
Line 21, delete "B1478" and insert -- B-478- --
Line 34, delete "m" and insert -- III --
Line 36, delete "1TT" and insert -- III --

Column 10,
Line 44, delete "Gin" and insert -- Gln --

Column 17,
Line 5, delete "m" and insert -- III --

Column 20,
Line 56, delete "GBbeA" and insert -- GBbcA --
Line 63, after "by" delete "."

Column 21,
Line 32, delete "II" and insert -- III --
Line 42, delete "HI" and insert -- III --

UNITED STATES PATENT AND TRADEMARK OFFICE
CERTIFICATE OF CORRECTION

PATENT NO. : 6,582,950 B1
DATED : June 24, 2003
INVENTOR(S) : Smith et al.

It is certified that error appears in the above-identified patent and that said Letters Patent is hereby corrected as shown below:

Column 29,
Line 59, after "by" delete "."

Signed and Sealed this

Eighteenth Day of November, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 20
<212> TYPE: PRT
<213> ORGANISM: Streptococcus agalactiae

<400> SEQUENCE: 1

```
Asp Gln Thr Thr Ser Val Gln Val Asn Asn Gln Thr Gly Thr Ser Val
1               5                   10                  15

Asp Ala Ala Asn
            20
```

<210> SEQ ID NO 2
<211> LENGTH: 12
<212> TYPE: PRT
<213> ORGANISM: Streptococcus agalactiae

<400> SEQUENCE: 2

```
Ile Ala Thr Gln Gly Asn Tyr Thr Phe Ser His Lys
1               5                   10
```

<210> SEQ ID NO 3
<211> LENGTH: 12
<212> TYPE: PRT
<213> ORGANISM: Streptococcus agalactiae

<400> SEQUENCE: 3

```
Asn Tyr Asp Gln Val Leu His Ala Asp Gly Tyr Ser
1               5                   10
```

<210> SEQ ID NO 4
<211> LENGTH: 1163
<212> TYPE: DNA
<213> ORGANISM: Streptococcus agalactiae

<400> SEQUENCE: 4

```
taatcagaca ggcactagtg tggatgctaa taattcttcc aatgagacaa gtgcgtcaag      60
tgtgattact tccaataatg atagtgttca agcgtctgat aaagttgtaa atagtcaaaa     120
tacggcaaca aaggacatta ctactccttt agtagagaca aagccaatgg tggaaaaaac     180
attacctgaa caagggaatt atgtttatag caaagaaacc gaggtgaaaa atacaccttc     240
aaaatcagcc ccagtagctt tctatgcaaa gaaaggtgat aaagtttctt atgaccaagt     300
atttaataaa gataatgtga aatggatttc atataagtct tttggtggcg tacgtcgata     360
cgcagctatt gagtcactag atccatcagg aggttcagag actaaagcac ctactcctgt     420
aacaaattca ggaagcaata atcaagagaa aatagcaacg caaggaaatt atacattttc     480
acataaagta gaagtaaaaa atgaagctaa ggtagcgagt ccaactcaat ttacattgga     540
caaaggagac agaattttt acgaccaaat actaactatt gaaggaaatc agtggttatc     600
ttataaatca ttcaatggtg ttcgtcgttt tgttttgcta ggtaaagcat cttcagtaga     660
aaaaactgaa gataagaaa aagtgtctcc tcaaccacaa gcccgtatta ctaaaactgg     720
tagactgact atttctaacg aaacaactac aggttttgat attttaatta cgaatattaa     780
```

-continued

```
agatgataac ggtatcgctg ctgttaaggt accggtttgg actgaacaag gagggcaaga        840
tgatattaaa tggtatacag ctgtaactac tggggatggc aactacaaag tagctgtatc        900
atttgctgac cataagaatg agaagggtct ttataatatt catttatact accaagaagc        960
tagtgggaca cttgtaggtg taacaggaac taaagtgaca gtagctggaa ctaattcttc       1020
tcaagaacct attgaaaatg gtttaccaaa gactggtgtt tataatatta tcggaagtac       1080
tgaagtaaaa aatgaagcta aaatatcaag tcagacccaa tttactttag aaaaaggtga       1140
caaaataaat gacaagtttc ccc                                               1163
```

<210> SEQ ID NO 5
<211> LENGTH: 445
<212> TYPE: PRT
<213> ORGANISM: Streptococcus agalactiae

<400> SEQUENCE: 5

```
Met Val Thr Ser Pro Val Phe Ala Asp Gln Thr Thr Ser Val Gln Val
1               5                   10                  15

Asn Asn Gln Thr Gly Thr Ser Val Asp Ala Asn Asn Ser Ser Asn Glu
            20                  25                  30

Thr Ser Ala Ser Ser Val Ile Thr Ser Asn Asn Asp Ser Val Gln Ala
        35                  40                  45

Ser Asp Lys Val Val Asn Ser Gln Asn Thr Ala Thr Lys Asp Ile Thr
    50                  55                  60

Thr Pro Leu Val Glu Thr Lys Pro Met Val Glu Lys Thr Leu Pro Glu
65                  70                  75                  80

Gln Gly Asn Tyr Val Tyr Ser Lys Glu Thr Glu Val Lys Asn Thr Pro
                85                  90                  95

Ser Lys Ser Ala Pro Val Ala Phe Tyr Ala Lys Lys Gly Asp Lys Val
            100                 105                 110

Phe Tyr Asp Gln Val Phe Asn Lys Asp Asn Val Lys Trp Ile Ser Tyr
        115                 120                 125

Lys Ser Phe Gly Gly Val Arg Arg Tyr Ala Ala Ile Glu Ser Leu Asp
    130                 135                 140

Pro Ser Gly Gly Ser Glu Thr Lys Ala Pro Thr Pro Val Thr Asn Ser
145                 150                 155                 160

Gly Ser Asn Asn Gln Glu Lys Ile Ala Thr Gln Gly Asn Tyr Thr Phe
                165                 170                 175

Ser His Lys Val Glu Val Lys Asn Glu Ala Lys Val Ala Ser Pro Thr
            180                 185                 190

Gln Phe Thr Leu Asp Lys Gly Asp Arg Ile Phe Tyr Asp Gln Ile Leu
        195                 200                 205

Thr Ile Glu Gly Asn Gln Trp Leu Ser Tyr Lys Ser Phe Asn Gly Val
    210                 215                 220

Arg Arg Phe Val Leu Leu Gly Lys Ala Ser Ser Val Glu Lys Thr Glu
225                 230                 235                 240

Asp Lys Glu Lys Val Ser Pro Gln Pro Gln Ala Arg Ile Thr Lys Thr
                245                 250                 255

Gly Arg Leu Thr Ile Ser Asn Glu Thr Thr Gly Phe Asp Ile Leu
            260                 265                 270

Ile Thr Asn Ile Lys Asp Asp Asn Gly Ile Ala Ala Val Lys Val Pro
        275                 280                 285

Val Trp Thr Glu Gln Gly Gly Gln Asp Asp Ile Lys Trp Tyr Thr Ala
    290                 295                 300
```

-continued

```
Val Thr Thr Gly Asp Gly Asn Tyr Lys Val Ala Val Ser Phe Ala Asp
305                 310                 315                 320

His Lys Asn Glu Lys Gly Leu Tyr Asn Ile His Leu Tyr Tyr Gln Glu
            325                 330                 335

Ala Ser Gly Thr Leu Val Gly Val Thr Gly Lys Val Thr Val Ala
            340                 345                 350

Gly Thr Asn Ser Ser Gln Glu Pro Ile Glu Asn Gly Leu Pro Lys Thr
            355                 360                 365

Gly Val Tyr Asn Ile Ile Gly Ser Thr Glu Val Lys Asn Glu Ala Lys
        370                 375                 380

Ile Ser Ser Gln Thr Gln Phe Thr Leu Glu Lys Gly Asp Lys Ile Asn
385                 390                 395                 400

Tyr Asp Gln Val Leu Thr Ala Asp Gly Tyr Gln Trp Ile Ser Tyr Lys
                405                 410                 415

Ser Tyr Ser Gly Val Arg Arg Tyr Ile Pro Val Lys Lys Leu Thr Thr
            420                 425                 430

Ser Ser Glu Lys Ala Lys Asp Glu Ala Thr Lys Pro Thr
        435                 440                 445
```

<210> SEQ ID NO 6
<211> LENGTH: 1337
<212> TYPE: DNA
<213> ORGANISM: Streptococcus agalactiae

<400> SEQUENCE: 6

| | | | | | |
|---|---|---|---|---|---|
| atggtcacaa | gtcctgtttt | tgcggatcaa | actacatcgg | ttcaagttaa | taatcagaca | 60 |
| ggcactagtg | tggatgctaa | taattcttcc | aatgagacaa | gtgcgtcaag | tgtgattact | 120 |
| tccaataatg | atagtgttca | agcgtctgat | aaagttgtaa | atagtcaaaa | tacggcaaca | 180 |
| aaggacatta | ctactccttt | agtagagaca | agccaatgg | tggaaaaaac | attacctgaa | 240 |
| caagggaatt | atgtttatag | caaagaaacc | gaggtgaaaa | atacaccttc | aaaatcagcc | 300 |
| ccagtagctt | tctatgcaaa | gaaaggtgat | aaagttttct | atgaccaagt | atttaataaa | 360 |
| gataatgtga | atggattttc | atataagtct | tttggtggcg | tacgtcgata | cgcagctatt | 420 |
| gagtcactag | atccatcagg | aggttcagag | actaaagcac | ctactcctgt | aacaaattca | 480 |
| ggaagcaata | atcaagagaa | aatagcaacg | cagggaaatt | atacattttc | acataaagta | 540 |
| gaagtaaaaa | atgaagctaa | ggtagcgagt | ccaactcaat | ttacattgga | caaaggagac | 600 |
| agaattttt | acgaccaaat | actaactatt | gaaggaaatc | agtggttatc | ttataaatca | 660 |
| ttcaatggtg | ttcgtcgttt | tgttttgcta | ggtaaagcat | cttcagtaga | aaaaactgaa | 720 |
| gataaagaaa | aagtgtctcc | tcaaccacaa | gcccgtatta | ctaaaactgg | tagactgact | 780 |
| atttctaacg | aaacaactac | aggttttgat | attttaatta | cgaatattaa | agatgataac | 840 |
| ggtatcgctg | ctgttaaggt | accggtttgg | actgaacaag | gagggcaaga | tgatattaaa | 900 |
| tggtatacag | ctgtaactac | tggggatggc | aactacaaag | tagctgtatc | atttgctgac | 960 |
| cataagaatg | agaagggtct | ttataatatt | catttatact | accaagaagc | tagtgggaca | 1020 |
| cttgtaggtg | taacaggaac | taaagtgaca | gtagctggaa | ctaattcttc | tcaagaacct | 1080 |
| attgaaaatg | gtttaccaaa | gactggtgtt | tataatatta | tcggaagtac | tgaagtaaaa | 1140 |
| aatgaagcta | aaatatcaag | tcagacccaa | tttactttag | aaaaaggtga | caaaataaat | 1200 |
| tatgatcaag | tattgacagc | agatggttac | cagtggattt | cttacaaatc | ttatagtggt | 1260 |
| gttcgtcgct | atattcctgt | gaaaaagcta | actacaagta | gtgaaaaagc | gaaagatgag | 1320 |

```
gcgactaaac cgactag                                                      1337

<210> SEQ ID NO 7
<211> LENGTH: 23
<212> TYPE: DNA
<213> ORGANISM: Artificial Sequence
<220> FEATURE:
<223> OTHER INFORMATION: Primer
<221> NAME/KEY: modified_base
<222> LOCATION: (9)..(9)
<223> OTHER INFORMATION: i
<221> NAME/KEY: modified_base
<222> LOCATION: (12)..(12)
<223> OTHER INFORMATION: i
<221> NAME/KEY: modified_base
<222> LOCATION: (15)..(15)
<223> OTHER INFORMATION: i
<221> NAME/KEY: modified_base
<222> LOCATION: (18)..(18)
<223> OTHER INFORMATION: i

<400> SEQUENCE: 7
gaycaracna cnwsngtnca rgt                                                 23

<210> SEQ ID NO 8
<211> LENGTH: 29
<212> TYPE: DNA
<213> ORGANISM: Artificial Sequence
<220> FEATURE:
<223> OTHER INFORMATION: Primer
<221> NAME/KEY: modified_base
<222> LOCATION: (6)..(6)
<223> OTHER INFORMATION: i
<221> NAME/KEY: modified_base
<222> LOCATION: (9)..(12)
<223> OTHER INFORMATION: i
<221> NAME/KEY: modified_base
<222> LOCATION: (15)..(15)
<223> OTHER INFORMATION: i

<400> SEQUENCE: 8
ccrtcngcnn nnarnacytg rtcrtartt                                           29
```